US006228646B1

(12) United States Patent
Hardy

(10) Patent No.: US 6,228,646 B1
(45) Date of Patent: May 8, 2001

(54) HELPER-FREE, TOTALLY DEFECTIVE ADENOVIRUS FOR GENE THERAPY

(75) Inventor: Stephen F. Hardy, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/812,618

(22) Filed: Mar. 7, 1997

Related U.S. Application Data

(60) Provisional application No. 60/013,220, filed on Mar. 7, 1996, and provisional application No. 60/026,908, filed on Sep. 27, 1996.

(51) Int. Cl.[7] .................................................. C12N 15/00

(52) U.S. Cl. ......................... 435/455; 435/456; 435/457; 435/320.1

(58) Field of Search ............................. 435/172.3, 320.1, 435/235.01, 440, 325, 455, 456, 457; 514/44

(56) References Cited

U.S. PATENT DOCUMENTS

| 4,959,317 | 9/1990 | Sauer | 435/172.3 |
|---|---|---|---|
| 5,919,676 | * 7/1999 | Graham et al. | 435/172.3 |

FOREIGN PATENT DOCUMENTS

| 300 422 | 7/1988 | (EP) . |
|---|---|---|
| WO 91/09957 | 7/1991 | (WO) . |
| WO 95/29993 | * 11/1995 | (WO) . |
| WO 96/40955 | 12/1996 | (WO) . |

OTHER PUBLICATIONS

Verma et al. Gene therapy promises, problems, and promises. Nature, vol. 389, pp. 239–242, Sep. 18, 1997.*
Kilby et al. Site–specific recombinases: tools for genome engineering. Trends in Genetics, vol. 9, No. 12, pp. 413–421, Dec. 1993.*
Anton, Martina and Graham, Frank L., "Site–Specific Recombination Mediated by an Adenvirus Vector Expressing the Cre Recombinase Protein: a Molecular Switch for Control of Gene Expression", *Journal of Virology*, vol. 69. No. 8:4600–4604 (Aug. 1995).
Bett, Andrew J., et al., "An Efficient and Flexible System for Construction of Adenovirus Vectors With Insertions or Deletions in Early Regions 1 and 3", *Proc.Natl.Acad.Sci.*, vol. 91:8802–8806 (1994).
Chinnadural, G., et al. "Physical Mapping of a Large–Plaque Mutation of Adenovirus Type 2", *Journal of Virology*, vol. 32, No. 2:623–628 (1979).
Engelhardt, John F., et al., "Prolonged Transgene Expression in Cotton Rat Lung With Recombinant Adenoviruses Defective in E2a", *Human Gene Therapy*, vol. 5: 1217–1229 (1994).

Englehardt, John F., et al., "Ablation of E2A in Recombionant Adenoviiruses Improves Transgene Persistence and Decreases Inflammatory Response in Mouse Liver", *Proc.Natl.Acad.Sci.*, vol. 91:6196–6200 (1994).
Engelhardt, John F., et al., "Adenovirus–Mediated Transfer of the CFTR Gene to Lung of Nonhuman Primates: Biological Efficacy Study", *Human Gene Therapy*, vol. 4:759–769 (1993).
Fisher, Krishna J., et al., "Recombinant Adenovirus Deleted of all Viral Genes for Gene Therapy of Cystic Fibrosis", *J. Virology*, vol. 217:11–22 (1996).
Grable, Maria and Hearing, Patrick, "Adenovirus Type 5 Packaging Domain is Composed of a Repeated Element That is Functionally Redundant", *Journal of Virology*, vol. 64, No. 5:2047–2056 (1990).
Grable, Maria and Hearing, Patrick, "cis and trans Requirements for the Slective Packaging of Adenovirus Type 5 DNA", *Journal of Virology*, vol. 66 No. 2:723–731 (1992).
Graham, F.L., and Van Der Eb, A.J., "A New Technique for the Assay of Infectivity of Human Adenovirus 5 DNA", *Virology*, vol. 52:456–467 (1973).
Hamilton, D.L. and Abremski, K., "Site–Specific Recombination by the Bacteriophage P1 lox–Cre System", *J.Mol.Biol.*, vol. 178:481–486 (1984).
Hoess, R.H. and Abremski, K., "The Cre–lox Recombination System", *Nuc.Acids.Mol.Biol.*, vol. 4:99–109 (1990).
Hoess, Ronald H., et al., "The Role of loxP Spacer Region in P1 Site–Specific Recombination", *Nuc.Acids Research*, vol. 14, No. 5:2287–2300 (1986).
Kochanek, Stefan, et al., "A New Adenoviral Vector: Replacement of all Viral Coding Sequences with 28kb of DNA Independently Expressing Both Full–Length Dystrophin and β–Galactosidase", *Proc.Natl.Acad.Sci.*, vol. 93:5731–5736 (1996).
Kremer, E.J. and Perricaudet, M., "Adenovirus and Adeno–Associated Virus Mediated Gene Transfer", *British Med.Bull.*, vol. 51:31–44 (1995).
Lieber, Andre, et al., "Recombinant Adenoviruses With Large deletions Generated by Cre–Mediated Excision Exhibit Different Biological Properties Compared With First–Generation Vectors in Vitro and In Vivo", *Journal of Virology*, vol. 70, No. 12:8944–8960 (1996).

(List continued on next page.)

*Primary Examiner*—Deborah Crouch
(74) *Attorney, Agent, or Firm*—Mandel and Adriano

(57) ABSTRACT

A method for producing in vivo packaged recombinant adenovirus vectors is provided. The recombinant Ad vectors do not contain any Adenovirus genes and are therefore useful for gene therapy. The recombinant Adenovirus vectors are packaged in vivo using a helper virus which is itself very inefficiently packaged, providing a recombinant viral preparation with very little or no contamination with helper virus. In particular, the method makes use of a helper virus in which the packaging site can be easily excised in vivo by recombination mediated by a recombinase. The helper virus is also useful for the in vivo construction of new recombinant adenovirus vectors containing substitutions in the E1 or other adenoviral region.

26 Claims, 16 Drawing Sheets

OTHER PUBLICATIONS

McCray, Paul B., et al., "Adenoviral–Mediated Gene Transfer for Fetal Pulmonary epithia in Vitro and in Vivo", *J.Clin.Invest.*, vol. 95:2620–2632 (1995).

McGrory, et al., "Simple Technique for the Rescue of Early Region 1 Mutations Into Infectious Human Adenovirus Type 5", *Virology*, vol. 163:614–617 (1988).

Mitani, Kohnosuke, et al., "Rescue, Propagation, and Partial Purification of Helper Virus–Dependent Adenovirus Vector", *Proc.Natl.Acad.Sci.USA*, vol. 92:3854–3858 (1995).

O'Gorman, Stephen, et al., "Recombinase–Mediated Gene Activation and Site–Specific Integration in Mammalian Cells", *Science*, vol. 251:1351–1355 (1991).

Parks, Robin J., et al., "A Helper–Dependent Adenovirus vector system: Removal of Helper Virus by Cre–mediated Excision of the Viral Packaging Signal", *Proc.Natl.Acad..Sci.USA*, vol. 93:13565–13570 (1996).

Rosenfeld, Melissa, et al., "In Vivo Transfer of the Human Cystic Fibrosis Transmembrane Conductance Regulator Gene to the Airway Epithelium", *Cell*, vol. 68:143–155 (1992).

Sauer, Brian, "Functional Expression of the cre–lox Site–Specific recombination System in the Yeast *Saccharomyces cerevisiae*", *Molecular and Cellular Biology*, vol. 7, No. 6:2087–2096 (1987).

Sauer, Brian, "Manipulation of Transgenes by Site–Specific Recombination: Use of Cre Recombinase", *Methods in Enzymology*, vol. 225:890–900 (1993).

Sauer, Brian and Henderson, Nancy, "Cre–stimulated Recombination at loxP–Containing DNA Sequences Placed Into the Mammalian Genome", *Nucleic Acids Research*, vol. 17, No. 1:147–161 (1989).

Sauer, Brian and Henderson, Nancy, "Targeted Insertion of Exogenous DNA Into the Eukaryotic Genome by the Cre Recombinase", *The New Biologist*, vol. 2, No. 5:441–449 (1990).

Sauer, Brian and Henderson, Nancy, "Site–Specific DNA Recombination In mammalian cells by the Cre Recombinase of Bacteriophage P1", *Proc.Natl.Acad.Sci.USA*, vol. 85:5166–5170 (1988).

Sharp, Phillip A., "Adenovirus Transcription", pp. 173–204.

Smith, Theodore A.G., et al., "Adenovirus Mediated Expression of Therapeutic Plasma Levels of Human Factor IX in Mice", *Nature Genetics*, vol. 5:397–402 (1993).

Yang, Yiping, et al., "Cellular and Humoral Immune Response to viral Antigens Create Barriers to Lung–Directed Gene Therapy With Recombinant Adenoviruses", *Journal of Virology*, vol. 69, No. 4:2004–2015 (1995).

Yang, Yiping, et al., "Cellular Immunity to Viral Antigens Limits El–Deleted Adenoviruses for Gene Therapy", *Proc..Natl.Acad.Sci,USA*, vol. 91:4407–4411 (1994).

Yang, Yiping, et al., "Inactivation of E2a in Recombinant Adenoviruses Improves the Prospect for Gene Therapy in Cystic Fibrosis", *Nature Genentics*, vol. 7:362–369 (1994).

Yang, Yiping, et al., "Cellular and Humoral Immune responses to Viral Antigens Create Barriers to Lung–Directed Gene Therapy With Recombinant Adenoviruses", *Journal of Virology*, vol. 69, No. 4:2004–2015 (1995).

Hecker et al., "In Vivo Expression of Full–Length Human Dystrophin from Adenoviral Vectors Deleted of All Viral Genes, " Human Gene therapy, vol. 7:1907–1914 (Oct. 1, 1996).

Hardy et al., "Construction of Adenovirus Vectors through Cre–lox Recombination," Journal of Virology, vol. 71 (3) :1842–1849 (1997).

* cited by examiner

LOX SITES

| | | | | |
|---|---|---|---|---|
| lox P | (SEQ ID NO:1) | ATAACTTCGTATA | ATGTATGC | TATACGAAGTTAT |
| lox 511 | (SEQ ID NO:2) | ATAACTTCGTATA | ATGTATAC | TATACGAAGTTAT |
| lox 514 | (SEQ ID NO:3) | ATAACTTCGTATA | ATGTACGC | TATACGAAGTTAT |
| lox Psym | (SEQ ID NO:4) | ATAACTTCGTATA | ATGTACAT | TATACGAAGTTAT |

FIG. 2

Selections for gutless virus.

A) Cell sorting by detection of a passive marker.
marker genes: lacZ, AP, GFP, CD24, truncated NGFR

TITRATION OF GUTLESS + HELPER VIRUSES (1::1) ON CRE8 CELLS

PHASING IN CRE/LOX RECOMBINATION

| | turns | 293/CRE |
|---|---|---|
| Ψ9 | 28.6 | 2.4 |
| Ψ9+17 | 30.3 | 4.5 |

Ψ11 PACKAGING IN 293 AND CRE8 CELLS

M 293 CRE8

HELPER-FREE, TOTALLY DEFECTIVE ADENOVIRUS FOR GENE THERAPY

This application claims the benefit of U.S. Provisional Applications No. 60/013,220, filed Mar. 7, 1996 and No. 60/026,908, filed Sep. 27, 1996.

ACKNOWLEDGEMENTS

This invention was made with Government support under Grants Nos. P01-NS16033 and R01-NS13521, awarded by the National Institutes of Health. The U.S. Government has certain rights in this invention.

INTRODUCTION

BACKGROUND

Adenoviruses (Ads) belong to the family Adenoviridae and the human Ads belong to the genera Mastadenovirus. Human Ad infections are found worldwide. Ads were initially characterized in 1953 by Rowe et al. when trying to cultivate epithelial cells from the adenoids. The 47 different serotypes are grouped (A–F) according to their ability to cause tumours in newborn hamsters. Respiratory epithelial cells are the primary target for Ads in vivo. 5% of the acute respiratory diseases in children under the age of 5 are due to Ads. Other sites of infection include the eye, the gastrointestinal tract and the urinary tract. Many Ad infections are subclinical and only result in antibody formation.

Three loosely defined sets of protein exist in the mature Ad: proteins that form the outer coat of the capsid, scaffolding proteins that hold the capsid together and DNA-binding proteins. The diameter of the icosahedral-shaped capsid varies from 65 to 80 nm depending on the serotype. The capsid is composed of a total of 720 hexon and 60 penton subunit proteins, 360 monomers of polypeptide VI, 240 monomers of polypeptide IX, and 60 trimeric fibre proteins.

Bound to the penton subunits and protruding from the capsid is the fibre protein which mediates the initial attachment of the virus to a target cell. Polypeptides IX, IIIa, and VI form the scaffolding which holds the capsid together. Polypeptide IX stabilizes the packing of adjacent hexons in the capsid, polypeptide IIIa spans the capsid to link hexons of adjacent faces, and polypeptide VI connects the structural proteins to the core. The core consists of DNA associated with polypeptides V, VII, $\mu$ and the terminal protein.

Ads contain double stranded DNA as their genetic material. The base composition of the 47 characterized serotypes (Ad1–Ad47) varies in the percent G+C content and in the length of the genome (approximately 36 kb) and of the inverted terminal repeats (100–140 bp). The genome is covalently linked at each 5' end to individual 55 kd terminal proteins, which associate with each other to circularize the DNA upon lysis of the virion.

The Ad genome is functionally divided into 2 major non-contiguous overlapping regions, early and late, based on the time of transcription after infection. The early regions are defined as those that are transcribed before the onset of viral DNA synthesis. The switch from early to late gene expression takes place about 7 hours after infection. The terms early and late are not to be taken too literally as some early regions are still transcribed after DNA synthesis has begun.

There are 6 distinct early regions; E1a, E1b, E2a, E2b, E3, and E4, each (except for the E2a–b region) with individual promoters, and one late region, which is under the control of the major late promoter, with 5 well characterized coding units (L1–L5). There are also other minor intermediate and/or late transcriptional regions that are less well characterized, including the region encoding the viral-associated (VA) RNAs. Each early and late region appears to contain a cassette of genes coding for polypeptides with related functions. Each region is transcribed initially as a single RNA which is then spliced into the mature mRNAs. More than 30 different mature RNA transcripts have been identified in Ad2, one of the most studied serotypes.

Once the viral DNA is inside the nucleus, transcription is initiated from the viral E1a promoter. This is the only viral region that must be transcribed without the aid of viral-encoded trans-activators. There are other regions that are also transcribed immediately after cell infection but to a lesser extent, suggesting that the E1 region is not the only region capable of being transcribed without viral-encoded transcription factors. The E1a region codes for more than six polypeptides. One of the polypeptides from this region, a 51 kd protein, transactivates transcription of the other early regions and amplifies viral gene expression. The E1b region codes for three polypeptides. The large E1b protein (55 kd), in association with the E4 34 kd protein, forms a nuclear complex and quickly halts cellular protein synthesis during lytic infections. This 55 kd polypeptide also interacts with p53 and directly inhibits its function. A 19 kd transactivating protein encoded by the E1B region is essential to transform primary cultures. The oncogenicity of Ads in new-born rodents requires the E1 region. Similarly, when the E1 region is transfected into primary cell cultures, cell transformation occurs. Only the E1a region gene product is needed to immortalize cell cultures.

The E2a and E2b regions code for proteins directly involved in replication, i.e., the viral DNA polymerase, the pre-terminal protein and DNA binding proteins. In the E3 region, the 9 predicted proteins are not required for Ad replication in cultured cells. Of the 6 identified proteins, 4 partially characterized ones are involved in counteracting the immune system; a 19 kd glycoprotein, gp19k, prevents cytolysis by cytotoxic T lymphocytes (CTL); and a 14.7 kd and a 10.4 kd/14.5 kd complex prevent, by different methods, E1a induced tumour necrosis factor cytolysis. The E4 region appears to contain a cassette of genes whose products act to shutdown endogenous host gene expression and upregulate transcription from the E2 and late regions. Once viral DNA synthesis begins, the late genes, coding mainly for proteins involved in the structure and assembly of the virus particle, are expressed.

Recombinant human adenoviruses have attracted much attention of late because of their potential for gene therapy and gene transfer and for protein expression in mammalian cells. First-generation recombinant adenovirus vectors most often contain deletions in the E1a and/or E1b regions. The usefulness of such vectors for gene transfer has been demonstrated in mice, cotton rats and nonhuman primates (Engelhardt et al. Hum. Gene Ther. 4:759–769 1993; Rosenfeld et al. Cell 68:143–155 1992; Yang et al. Nat. Genet. 7:362–369 1994). A fundamental problem encountered in using these vectors for gene therapy, however, is that deletion of the E1 sequences alone is not sufficient to completely ablate expression of other early and late viral genes or to prevent replication of the viral DNA. Studies have indicated that these vectors express viral antigens which elicit destructive immune responses in the target cells (Yang et al. Proc. Natl Acad. Sci. 91:4407–4411 1994; Yang et al. Nat. Genet. 7:362–369; Yang et al. J. Virol. 69:2004–2015 1995). This immune response leads to loss of transgene expression and development of inflammation. In addition, there is indication that memory-type immune responses may substantially diminish the efficiency of gene transfer following a second and subsequent administrations of the recombinant vector (Kozarsky et al. J. Biol. Chem. 269:1–8 1994; Smith et al. Nat. Genet. 5:397–402 1993). Newer recombinant adenovirus vectors contain additional disabling mutations in other regions of the adenovirus genome, for example in E2a (Englehardt et al. Hum. Gene Ther. 5:1217–1229 1994; Englehardt et al. Proc. Natl Acad. Sci. 91:6196–6200) or E3 (Bett et al. Proc. Natl Acad. Sci. 91:8802–8806 1994). These vectors, although they express fewer viral proteins, do not completely eliminate adenoviral protein expression and so are subject to similar immune response problems as found with the earlier vectors.

In addition to the immune response problems associated with the use of the current adenovirus-based gene therapy vectors, only relatively small amounts of foreign DNA (that is, non-adenovirus DNA) can be accommodated in these vectors due to the size constraints of adenoviral packaging. Studies have shown that adenovirus virions can package up to approximately 105% of the wild type adenovirus genome length (the wild type adenovirus genome is between 35–36 kilobases). Recombinant vectors having deletions in the E1 region typically permit the insertion of less than 5 kb of foreign DNA. Recombinant vectors having additional deletions in E3 can accommodate inserts of up to about 8 kb.

Another serious problem inherent in the use of current recombinant adenovirus-based vectors is their ability to recombine with adenoviruses from natural sources to produce infections of wild type viruses.

It would be advantageous to develop a recombinant adenovirus vector that is incapable of producing any adenovirus proteins, that can accommodate large inserts of foreign DNA and that recombines only at low frequency or not at all with other adenoviruses. The present inventor has surprisingly found that recombinant adenovirus (rAd) vectors containing as little as 600 base pairs of adenovirus sequence can be replicated and packaged in vivo to produce infectious virions. Adenoviral factors necessary for the replication and packaging of the minimal rAd vectors are supplied in trans from a recombinant adenovirus helper vector of the present invention which is designed such that the packaging site is easily excisable in vivo by the use of the Cre/lox recombination system.

Cre/lox is a site-specific recombination system, originally discovered in bacteriophage P1, which consists of a recombinase protein (Cre) and the DNA recognition site of the recombinase (Hoess and Abremski in "Nucleic Acids and Molecular Biology", Eckstein and Lilley, eds., Vol. 4, p. 99 Springer-Verlag 1990). Cre (causes recombination) is a member of the Int family of recombinases (Argos et al. EMBO J. 5:433 1986) and has been shown to perform efficient recombination of lox sites (locus of X-ing over) not only in bacteria but also in eukaryotic cells (Sauer Mol. Cell. Biol. 7:2087 1987; Sauer and Henderson Proc. Natl Acad. Sci. 85:5166 1988). The Cre recombinase can efficiently excise DNA bracketed by lox sites from the chromosome. Two components are required for recombination: the Cre recombinase and an appropriate lox-containing substrate DNA. Several different lox sites have been identified to date, for example lox P, lox 511, lox 514 and lox Psym (Hoess et al. Nucl. Acids Res. 14:2287–2301 1986). The sequences of the various lox sites are similar in that they all contain the identical 13-base pair inverted repeats flanking an 8-base pair asymmetric core region in which the recombination occurs. It is the asymmetric core region that is responsible for the directionality of the site and for the variation among the different lox sites. Only lox sites having the same sequence are recombined by Cre. Recombination between two directly oriented lox sites results in excision of the intervening DNA as a circular molecule having a single lox site and leaves a single lox site at the point of excision. The intramolecular excision is in equilibrium with the reverse reaction, that is, with intermolecular insertion of a DNA molecule containing a lox site into the identical lox site remaining in the chromosome. The excision reaction is favored 20 to 1 over the insertion reaction. Recombination between two inversely oriented lox sites results in inversion rather than excision of the intervening DNA. Cre/lox has been used to remove unwanted DNA sequences from the genome (for example, selectable marker genes when no longer needed for selection), for designing recombination dependent switches to control gene expression (Sauer and Henderson Nucl. Acids Res. 17:147 1989) and to direct site-specific integration of lox vectors into a lox site previously placed into the chromosome (Sauer and Henderson New Biol. 2:441 1990).

Relevant Literature

Early experiments showed that it was possible to create defective adenoviruses which carried substitutions of all or part of the SV40 genome in tandem. The deletions included 16% to 29%, 29% to 75% and 75% to 96%, indicating that virtually all of the Ad virus could be substituted. (For a summary of these experiments see, *The Adenoviruses*, Harold S. Ginsberg, ed. Plenum Press, NY, 1984.)

Bett et al. have described an adenovirus vector containing deletions in both the E1 and E3 regions (Proc. Natl Acad. Sci. 91:8802–8806 (1994)). Mitani et al. (Proc. Natl Acad. Sci. 92:3854–3858 (1995)) have described a recombinant adenoviral vector which is deficient in E1 and contains a 7.23 kb deletion in an essential part of the viral genome carrying L1, L2, VA and TP. A marker gene was inserted in place of the deleted adenoviral DNA and the vector was replicated and packaged after tranfection of 293 cells using a wild type Ad2 virus as a helper. The helper virus was also replicated and packaged. The packaged viruses (wild type helper virus and recombinant virus) were partially separated by repeated CsCl gradient centrifugation.

Anton and Graham (J. Virol. 69:4600–4606 (1995)) have used Cre-mediated recombination of flanking lox P sites to turn on expression of a luciferase gene cloned into an adenoviral vector. The recombination of the lox sites resulted in the removal of a fragment of DNA between the luciferase coding sequence and the promoter. The Cre recombinase was supplied from a second adenoviral vector carrying the Cre gene under control of hCMV promoter.

U.S. Pat. No. 4,959,317 describes a method for producing site-specific recombination of DNA in eukaryotic cells using Cre-mediated recombination of lox sites. Cre-expressing eukaryotic cells are also disclosed. WO 91/09957 describes a method for producing site-specific recombination in plant cells using Cre-mediated recombination of lox sites. EP 0 300 422 describes a method for preparing recombinant animal viral vectors using Cre-mediated recombination between a lox P site on the virus and a lox P site on a plasmid.

SUMMARY OF THE INVENTION

It is an object of the present invention to provide therapeutic recombinant adenovirus-based (therapeutic rAd) vectors for gene therapy or for expression of foreign genes in mammalian cells. The therapeutic rAd vectors of the present invention contain a minimal amount of adenovirus DNA and are incapable of expressing any adenovirus antigens, i.e. "gutless". The therapeutic rAd vectors of the present invention provide the significant advantage of accommodating large inserts of foreign DNA while completely eliminating the problem of expressing adenoviral genes that result in an immunological response to viral proteins when a therapeutic rAd vector is used in gene therapy. In particular, the therapeutic rAd vector of the present invention comprises the adenovirus inverted terminal repeats, an adenovirus packaging site, one or more lox sites and up to 36–38 kb of foreign DNA. By "foreign" DNA is meant any genes or other DNA sequences that do not occur naturally in adenovirus.

The ability of these therapeutic rAd vectors to accommodate such large inserts of foreign DNA (up to 38 kb) permits construction of gene therapy vectors that contain and express extremely large individual genes or polynucleotide sequences as well as multiple genes or polynucleotide sequences. The foreign DNA that can be expressed can be any polynucleotide sequences that do not occur naturally in adenovirus, including the Duchenne Muscular Dystrophy (DMD) gene, all genes involved in dopamine synthesis (e.g. tyrosine hydroxylase, GPD cyclohydroxylase), Factor VIII, Factor IX, superoxide dismutase, GM-CSF (granulocyte-macrophage colony-stimulating factor), granulomatous disease (CGD), and multiple genes, including GM-CSF in combination with other cytokines (e.g. interferons (IFN-$\alpha$, IFN-$\beta$, IFN-$\gamma$), interleukins, M-CSF (macrophage colony-stimulating factor), tumor necrosis factors, growth factors (TGF-$\beta$(transforming growth factor-$\beta$) and PDGF (platelet-derived growth factor)), and including GM-CSF with MHC (major histocompatibility complex) genes. The ability to deliver expression products from extremely large sequences or multiple sequences provides a simple and efficient delivery system.

The present invention includes the discovery that the minimum size range for the rAd vectors is from 32 kb to 38 kb, as smaller rAd vectors (<32 kb) are unstable and not efficiently packaged. This discovery of the lower size limit for packaging efficiency permits increased stability, which is important for vectors intended for gene therapy and increased production efficiency, which can reduce manufacturing costs significantly. Thus, provided herein are methods of producing a rAd vector for gene therapy, comprising constructing a therapeutic rAd vector wherein said vector ranges in total size from 32 kb to 38 kb. The vectors of the invention include both plasmids as well as packaged recombinant viral and foreign DNA.

Because the therapeutic rAd vectors of the present invention do not express any adenovirus proteins, those adenovirus proteins that are required for the replication and packaging of the therapeutic rAd vectors of the present invention are supplied in trans by a helper recombinant adenovirus vector (helper rAd).

It is another object of the present invention to provide a helper recombinant adenovirus vector which is useful for the preparation of in vivo packaged therapeutic rAd vectors. The helper rAd vector of the present invention comprises adenovirus genes which encode proteins necessary for the replication and packaging of the therapeutic rAd vectors into therapeutic rAd virus particles. The helper rAd vector of the present invention additionally comprises an adenovirus packaging site flanked by at least one set of two identical lox sites in direct orientation. When the helper rAd of the present invention is grown in a host cell that produces Cre recombinase, the packaging site is excised by Cre-mediated recombination between the flanking lox sites. Since the presence of an adenovirus packaging site is absolutely required for packaging of the DNA into adenovirus virions, removal of the packaging site by excision prevents the helper rAd vector from being packaged. One of ordinary skill in the art will understand that the host cells useful in the invention can be any cell lines susceptible to adenovirus infection and capable of expressing a recombinase capable of mediating recombination between recombination sites. Any recombinase-expressing cell line and its corresponding recombination sites can be used, including, but not limited to, the FLP recombinase and its recombination site. See O'Gorman et al., Science 251:1351 (1991). The term recombinase includes any enzymes that mediate recombination between its corresponding recombination sites, which are nucleic acid sequences that are specifically recognized by the recombinase. One of ordinary skill in the art will readily appreciate that any examples describing cre-recombinase and lox sites can be substituted with any other recombinase and its corresponding recombination sites.

Generally, the helper rAd vector of the present invention comprises all of the adenovirus genes necessary to provide the replication and packaging functions but may contain less than all of the necessary genes if the proteins encoded by some of these adenovirus genes are supplied in other ways, for example, by the host cell. In particular, the helper rAd vector need not contain the adenovirus E1a and E1b regions if used in combination with a host cell that can supply E1a and E1b gene products. If such a cell line is used, the E1a gene promoter should be transcribed from a heterologous promoter. It is essential that the Ad packaging site in the E1a promoter enhancer is not present in the host cell line.

It is a further object of the present invention to provide a system and a method for preparing a substantially pure preparation of in vivo packaged therapeutic rAd vector particles. The method of the present invention comprises transfecting an appropriate host cell with therapeutic rAd vector DNA and helper rAd vector DNA. The transfected cells are cultured for a sufficient time to allow maximum production of the therapeutic rAd virus. The virus particles are harvested and used to infect fresh host cells either with or without the addition of a small amount of packaged helper rAd virus particles. The virus particles produced following infection are isolated and the infection process may be repeated. In the final step, Cre-expressing host cells are infected with the viral particles produced in the earlier infections. Infection of the Cre-expressing cells provides for selection against the helper rAd so that a substantially pure preparation of packaged therapeutic rAd vector particles is produced.

Cre-expressing mammalian host cell cultures are also provided.

Also provided are methods and systems for rapidly and efficiently generating new recombinant adenovirus vectors with substitutions in a adenoviral region. These methods and systems comprise a helper rAd vector, a replicating vector containing ITRs, and Ad packaging site, substitute DNA and a recombination site identical to at least one of the recombination sites in the helper rAd vector, and a recombinase-expressing host cell line. One of skill in the art will appreciate that the vectors can be either recombinant adenoviruses or plasmids. These methods and systems provide a simple and efficient alternative to existing overlap recombination techniques. A working stock of virus can be produced for initial experiments within 10 days. Moreover, substituted rAds can be generated in substantially pure form without need for plaque purification. This solves the problem of purifying the recombinant adenovirus vectors with substitutions away from the rAd helper vectors. Other advantages of these methods are that (a) viral sequences in plasmids are more stable and easier to prepare than viral DNA, which is under continuous selection during growth and (b) recombinase-mediated recombination enables use of a small replicating vector which is extremely easy to manipulate. One of ordinary skill in the art will appreciate that both replicating and nonreplicating vectors can be used in these methods and systems.

BRIEF DESCRIPTION OF THE DRAWINGS

FIG. 2. Nucleotide sequence of several different lox sites.

ITR=inverted terminal repeat; $P_{CMV}$=CMV promoter; $P_{E1a}$=E1a promoter; arrow following ITR indicate the orientation. The vertical lines to the right of the $P_{CMV}$ indicate restriction sites in the polylinker.

Figure 4:
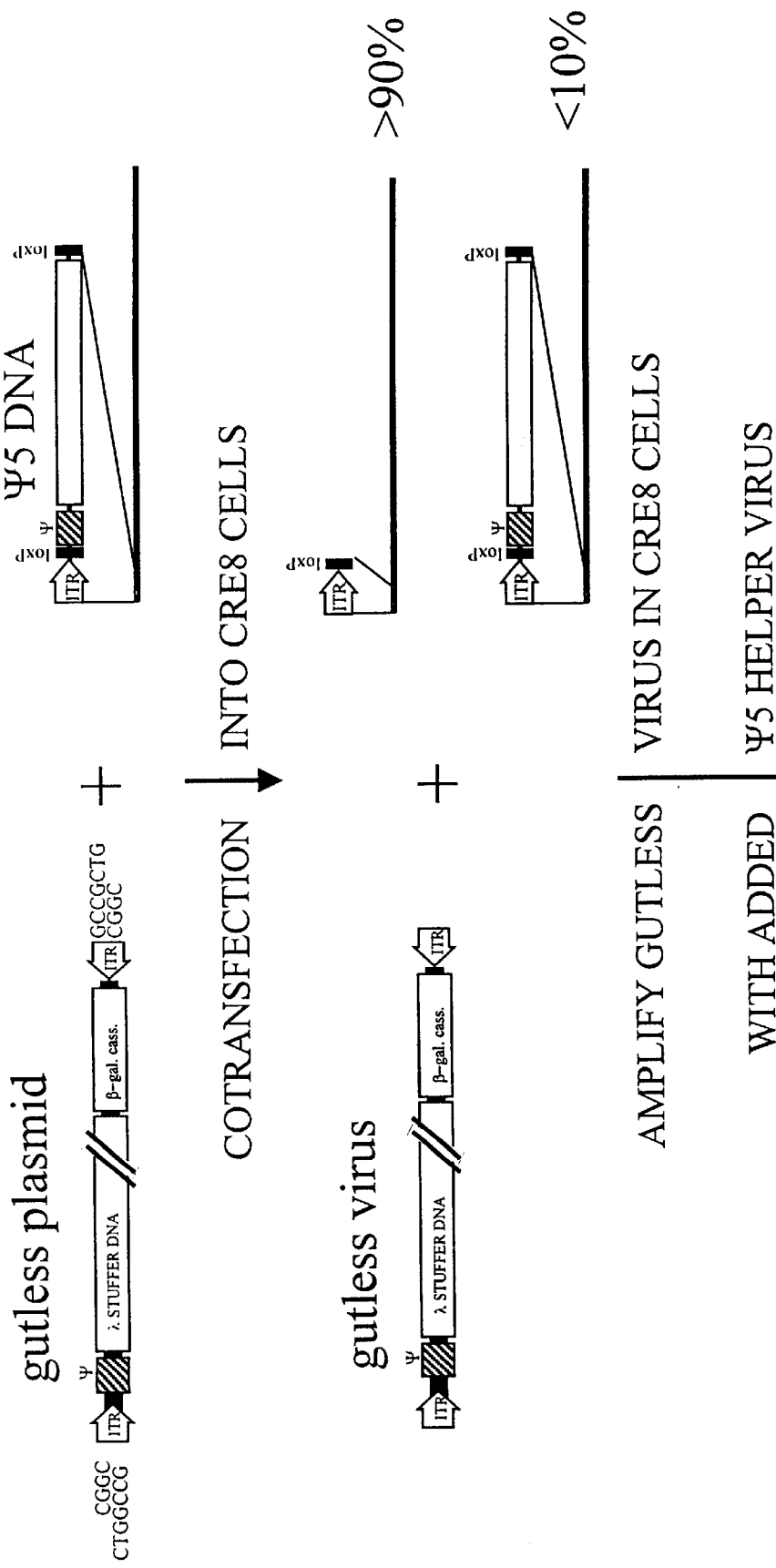

FIG. 4. Construction of a 'gutless' adenoviral vector. In the first step shuttle plasmid cleaved at the ITR is transfected into CRE8 cells with ψ5 DNA. The proteins from ψ5 convert the shuttle plasmid DNA to a molecule which is replicated by adenovirus DNA polymerase. The gutless virus is then encapsidated into adenovirus capsids. Several rounds of growth are necessary to amplify the gutless virus. At each round, more ψ5 virus is added to insure that all cells contain the helper virus.

Figure 5:
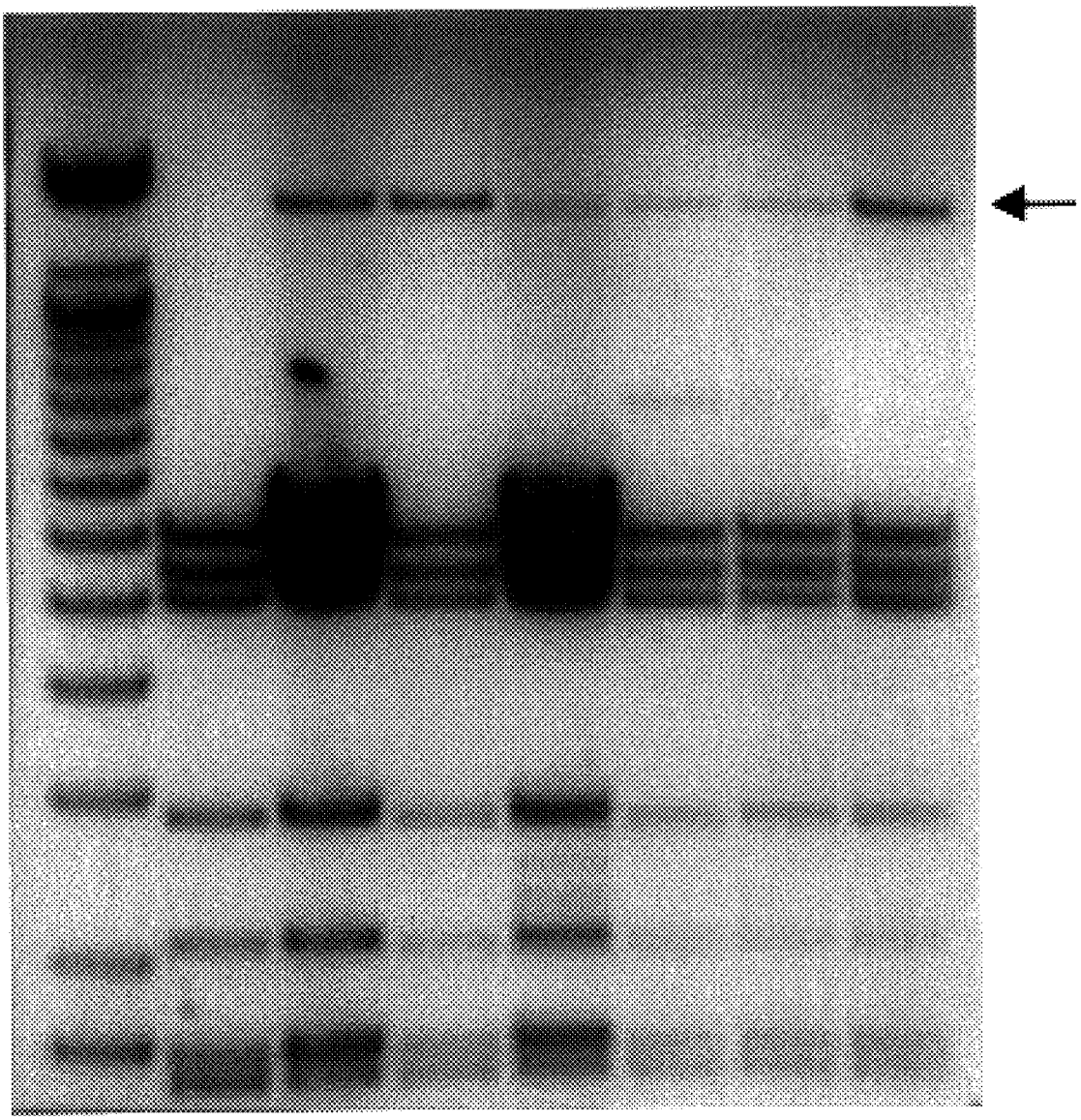

FIG. 5. is a gel showing a restriction analysis of packaged gutless and ψ5 DNA from infected CRE8 cells. The DNA was digested with Bgl II. There are no Bgl II sites in the loxAβ gutless virus. The lanes contain: M, 1 kb ladder+16.5 and 33.5 kb fragments; ψ5 DNA; lanes 1–6, isolates of loxAβ+ψ5. The arrow marks the position of loxAβ DNA.

Figure 6:
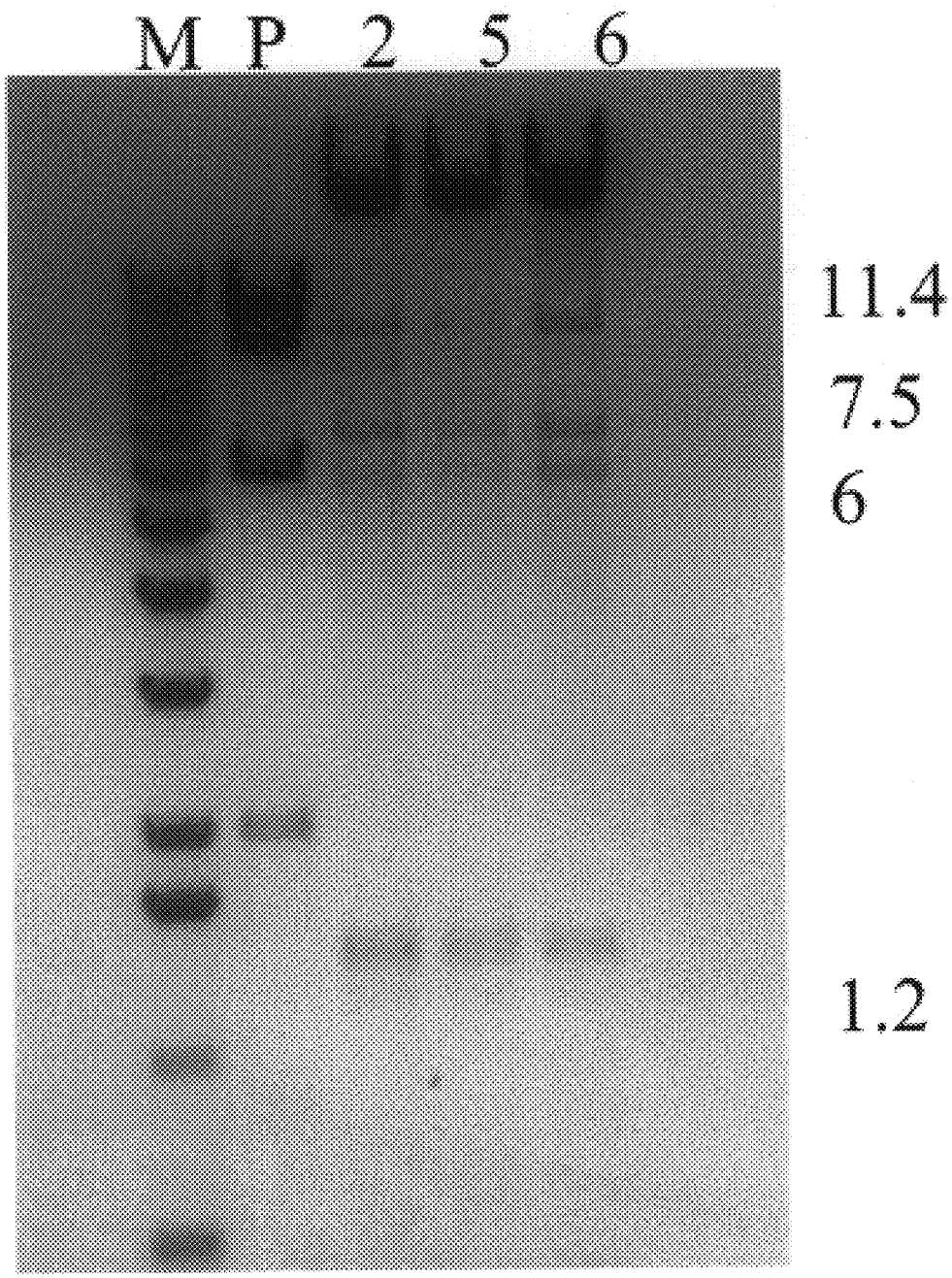

FIG. 6. is a gel showing a restriction analysis of loxAβ+ ψ5 DNA with ClaI. ψ5 DNA contains one site at base 1473. The predicted sizes of the loxAβ fragments are 0.5, 1.2, 6, 7.5, and 11.4 kb. The lanes contain: M, 1 kb ladder; P, ploxAβ cut with ClaI; isolates 2, 5 and 6 from part a cut with ClaI. (Many of the bands from ploxAβ do not match up with their cognate bands in loxAβ as the ClaI sites in the plasmid are methylated.)

Figure 7:
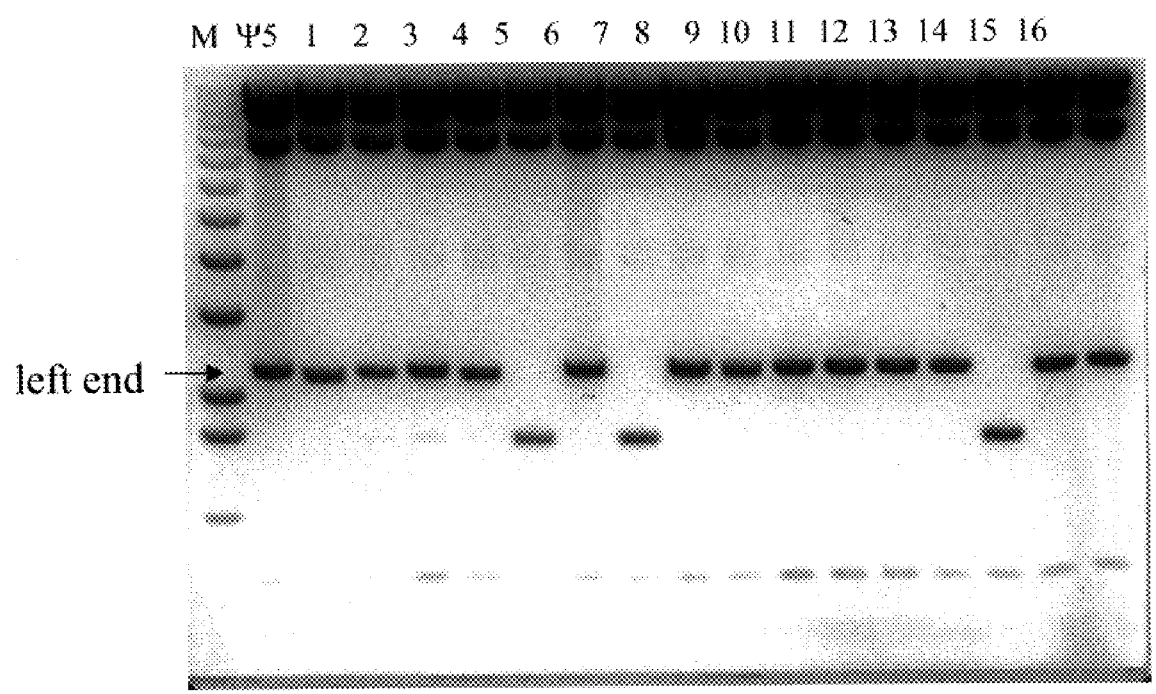

FIG. 7. Restriction analysis of ψ5 mutants with BsaBI. The position of the left end fragment from ψ5 is marked. The DNA was from 16 plaque isolates purified on 293 cells.

Figure 8A:
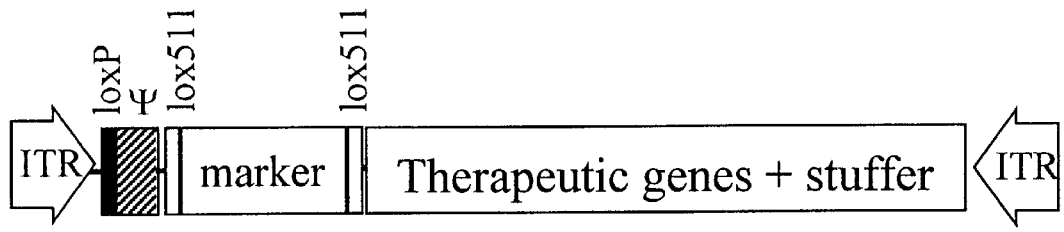
Figure 8A:
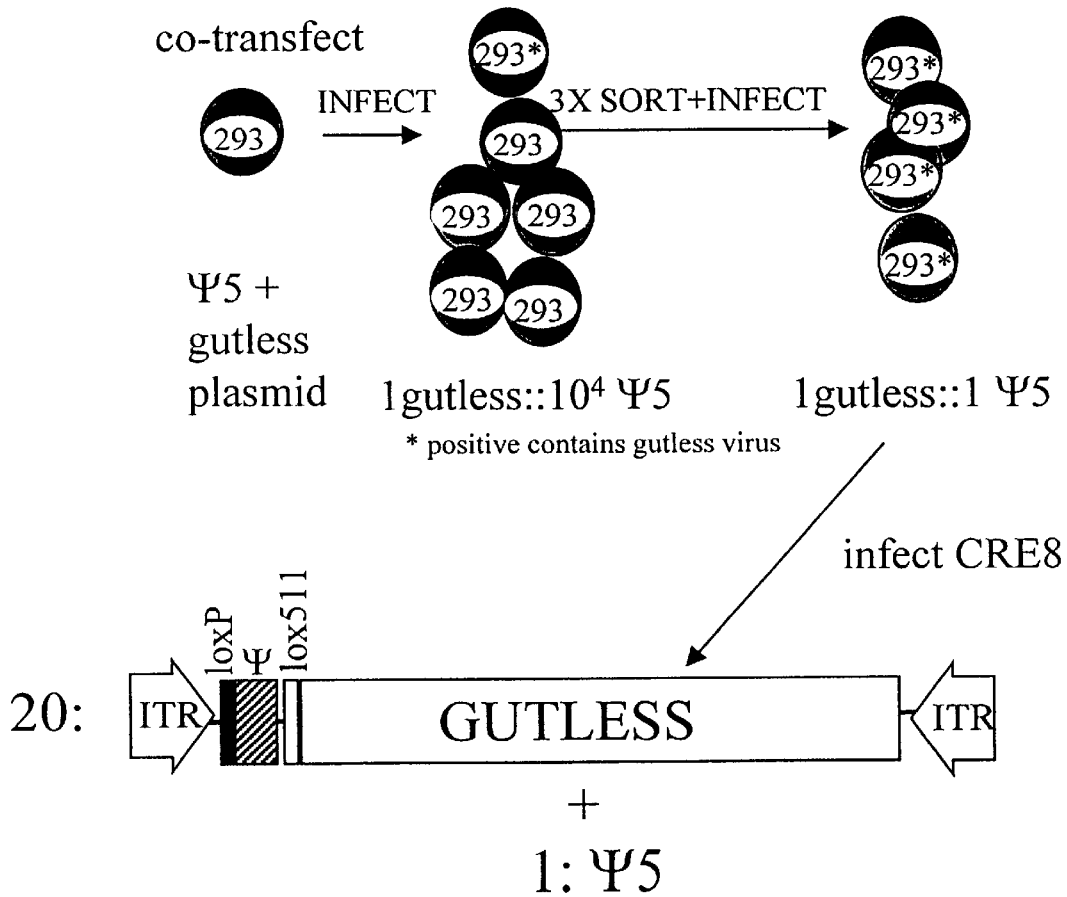
Figure 8B:
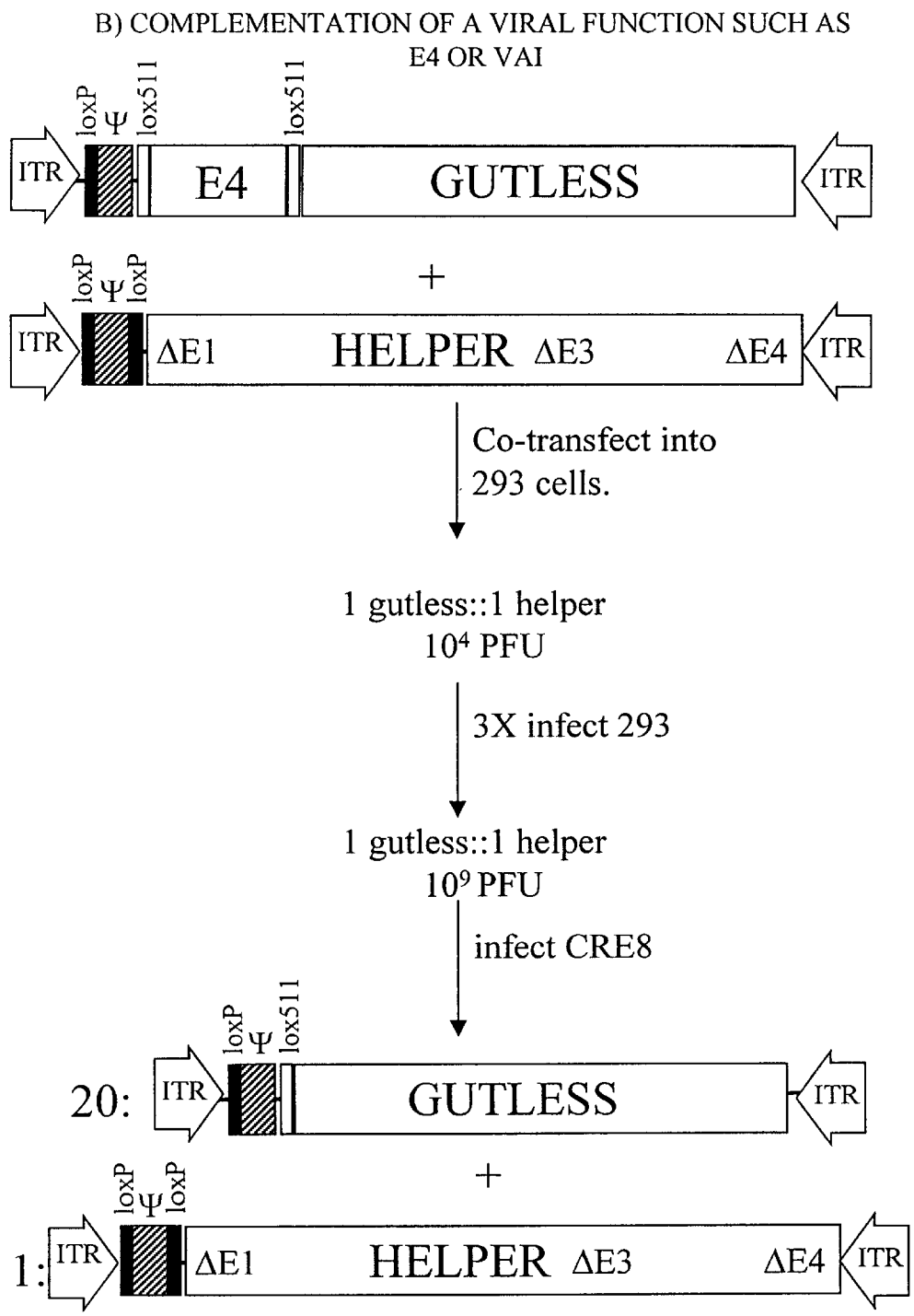
Figure 8C:
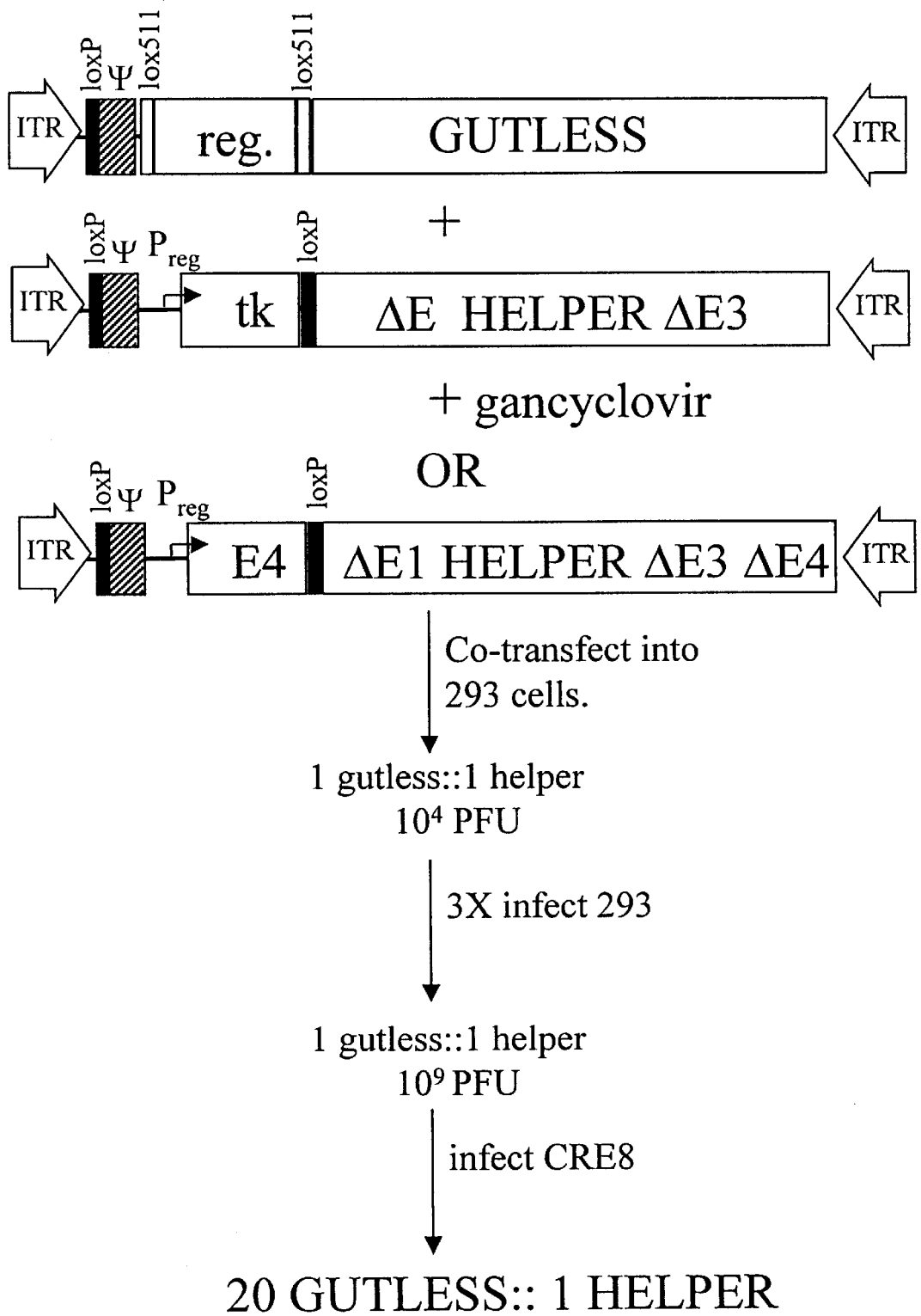

FIGS. 8A–8C. Methods for selecting gutless viruses. These methods allow for enrichment of gutless virus starting with a mixture containing about 0.5% gutless, and going to roughly 50%. In each arrangement, the gutless virus will be enriched based on expression of a gene in the virus. This selectable marker is flanked with lox511 sites and will be deleted from the gutless virus by growth in CRE8 cells for the final step of enrichment. The final enrichment takes the gutless virus concentration to 95% or more. ITR is the inverted terminal repeat of an adenovirus, ψ is the packaging site of an adenovirus. loxP and lox511 are loci of Cre recombinase directed recombination. loxP will recombine with loxP but not lox511 and visa versa.

FIG. 8A. Sorting for an expressed gene on the gutless virus. Here the selection is accomplished by mechanical means such as a cell sorter or by panning with an antibody. ψ5 is used as a helper virus. ψ5 DNA and gutless plasmid are cotransfected into 293 cells. The viruses are then grown together in 293 cells until the final passage through CRE8 cells.

FIG. 8B. Enrichment by complementation. An adenovirus gene is inserted between the lox511 sites in the gutless virus, E4 for example. A helper virus which is an E4 deleted version of ψ5 would then be cotransected into 293 cells. There should be no sequence in common flanking the E4 gene and the E4 deletion to minimize recombination between helper and gutless viruses. Only those cells containing both viruses will produce virus. The E4 deleted helper virus must be grown on a cell line complementing E1 and E4 genes.

FIG. 8C. A dominant selection in trans. A transcriptional regulator protein would be inserted between the lox511 sites in the gutless virus. The helper virus would be modified by placing a selectable marker in the E1 region controlled by the transcriptional regulator. The selection could be either positive or negative. For positive selection, a viral gene would be moved to the E1 region in the helper virus, fiber for example. Under this scenario, fiber gene transcription would require the regulatory protein from the gutless virus. For negative regulation, a poisonous gene such as herpes virus thymidine kinase (tk) would be inserted into the E1 region of the helper virus and gancyclovir added to the growth media. Here the regulatory protein would repress expression of the tk gene; otherwise the combination of tk and gancyclovir would poison viral DNA replication.

Figure 9:
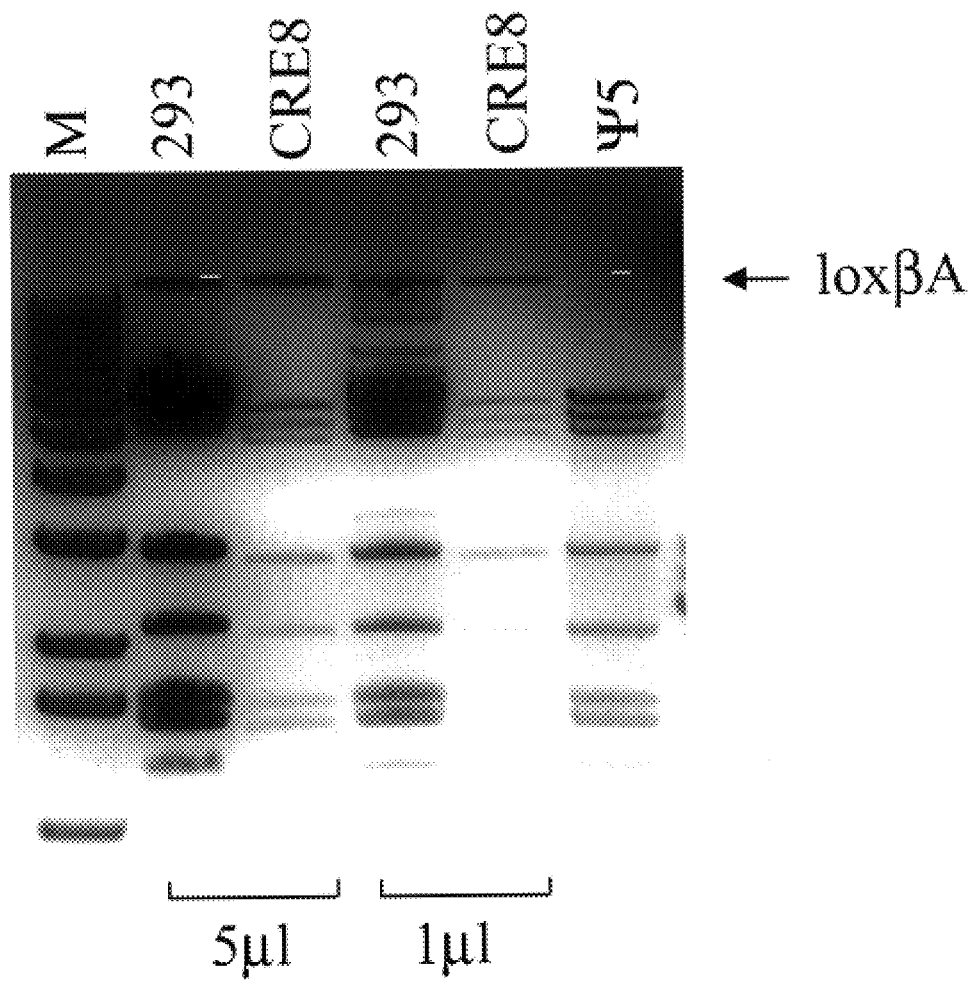

FIG. 9. Encapsidated loxβA 'gutless' and ψ5 helper viruses on 293 and CRE8 cells. Both DNA's were digested with BglII. Two different amounts of each sample is shown.

Figure 10A:
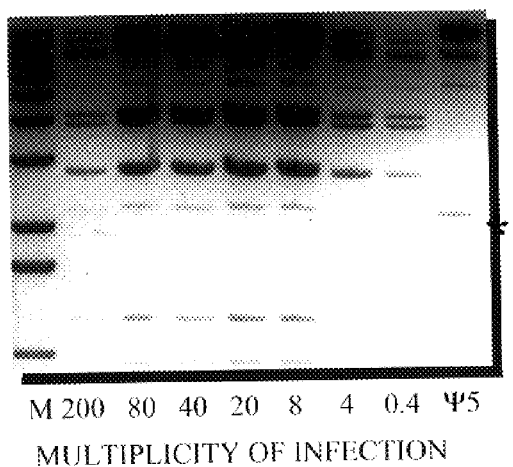
Figure 10B:
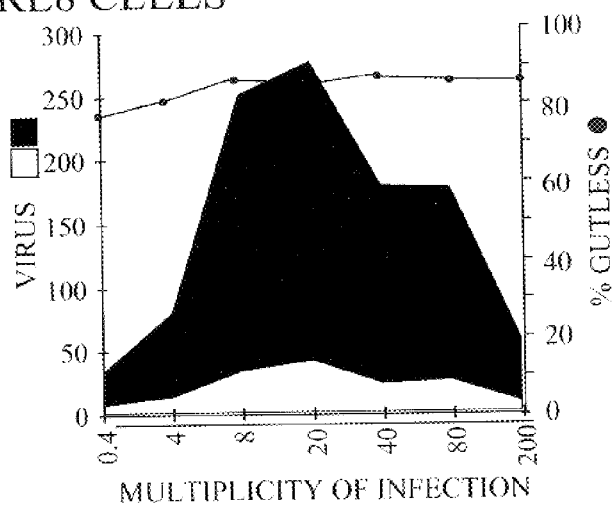

FIGS. 10A and 10B. Titration of a 1:1 mixture of loxβA and ψ5 on CRE8 cells. Packaged DNA was prepared from $10^7$ cells infected at moi's shown. The moi's are approximate and based on a single virus. FIG. 10A: The * on the gel marks the position of a 2.2 kb fragment unique to the helper virus. The major band migrating at 2.8 kb is from a pair of loxβA fragments. FIG. 10B: the graph shows the result of band intensities of the 2.2 and 2.8 kb bands, corrected for size and molarity.

Figure 11A:
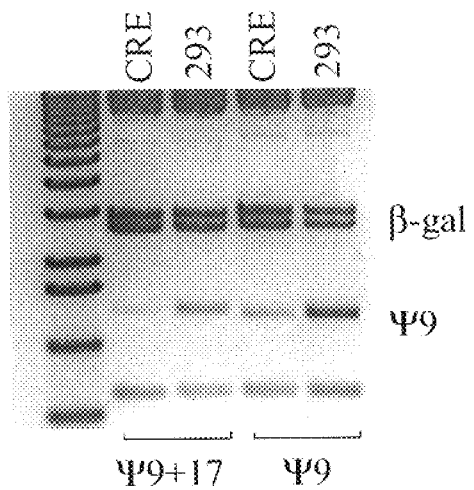
Figure 11B:
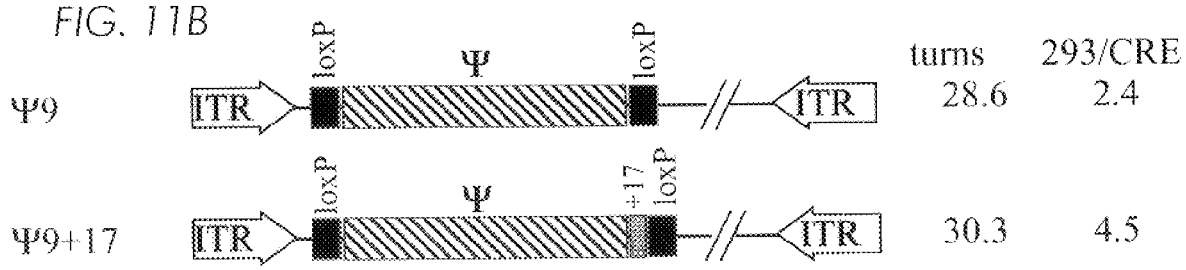

FIGS. 11A and 11B. Effect of DNA phasing on Cre/lox recombination. The ψ9 and ψ9+17 viruses were mixed with Ad β-gal virus and used to infect either 293 or CRE8 cells. Packaged DNA was prepared, digested with BsaBI, separated in an agarose gel and the intensities of the labeled bands were determined. FIG. 11A is a photograph of a gel showing BsaBI-digested DNAs. FIG. 11B is a diagram showing the phasing of the lox sites in the two different viruses, ψ9 and ψ9+17.

Figure 12A:
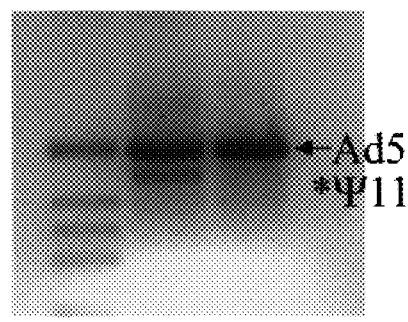
Figure 12B:
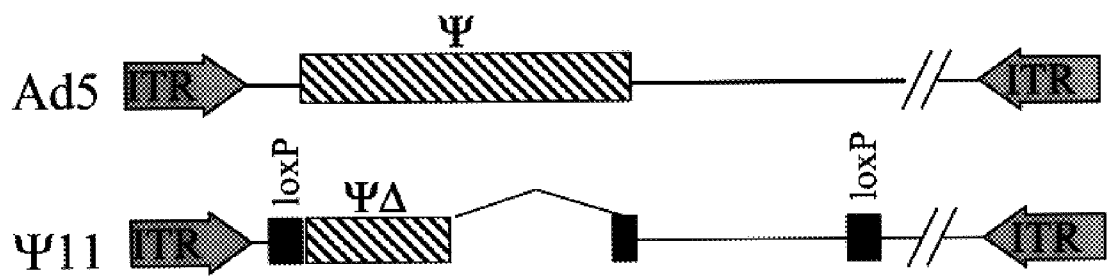

FIGS. 12A and 12B. Relative packaging efficiency of ψ11 virus. A mixture of 20 parts ψ11 to one part dl309 was used to infect $10^7$ either 293 or CRE8 cells at an moi of 10. Encapsidated DNA was prepared and ⅕ of the DNA was subjected to 10 cycles of PCR with primers which recognized both viral DNA's. There was no product when the viral DNA's were omitted. FIG. 12A is a gel showing the results. FIG. 12B is a diagram showing the structures of Ad5 and ψ11.

Figures 13A, 13B:
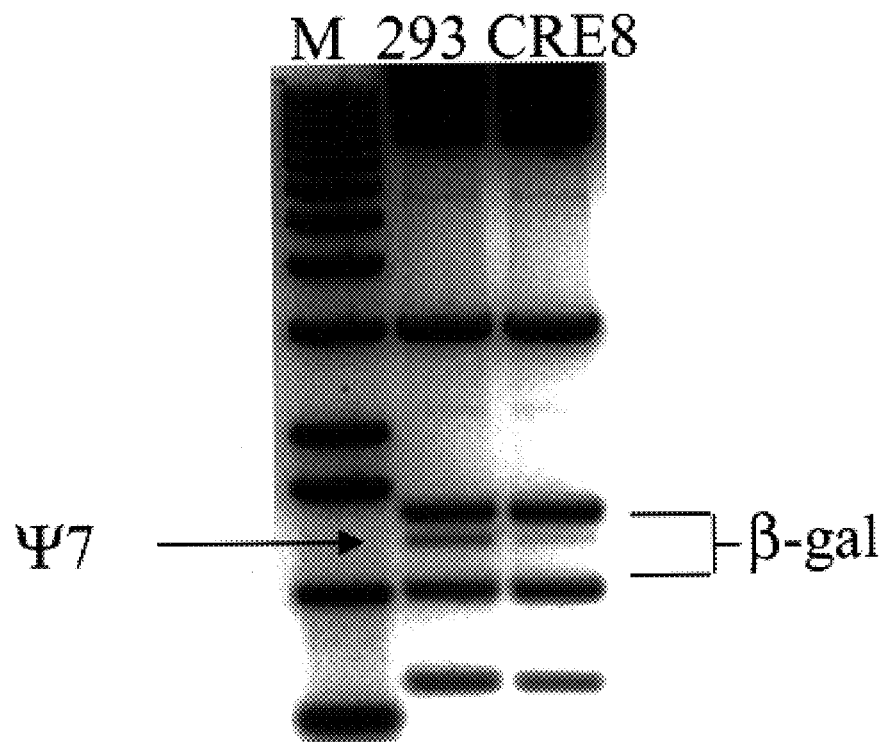

FIGS. 13A and 13B. Relative packaging efficiency of ψ7 virus. Equal numbers of particles of ψ7 and Ad tet β-gal were mixed and used to infect $10^7$ 293 or CRE8 cells at an moi of 10 for each virus. FIG. 13A: Packaged DNA was digested with BsaBI, separated and the intensities of the left end fragments were determined. FIG. 13B: In a measurement of the relative encapsidation efficiency, ψ7 was encapsidated at 30 and 5.9% of a similar virus with a normal Ad5 packaging site when grown in 293 and CRE8 cells respectively.

Figure 14:
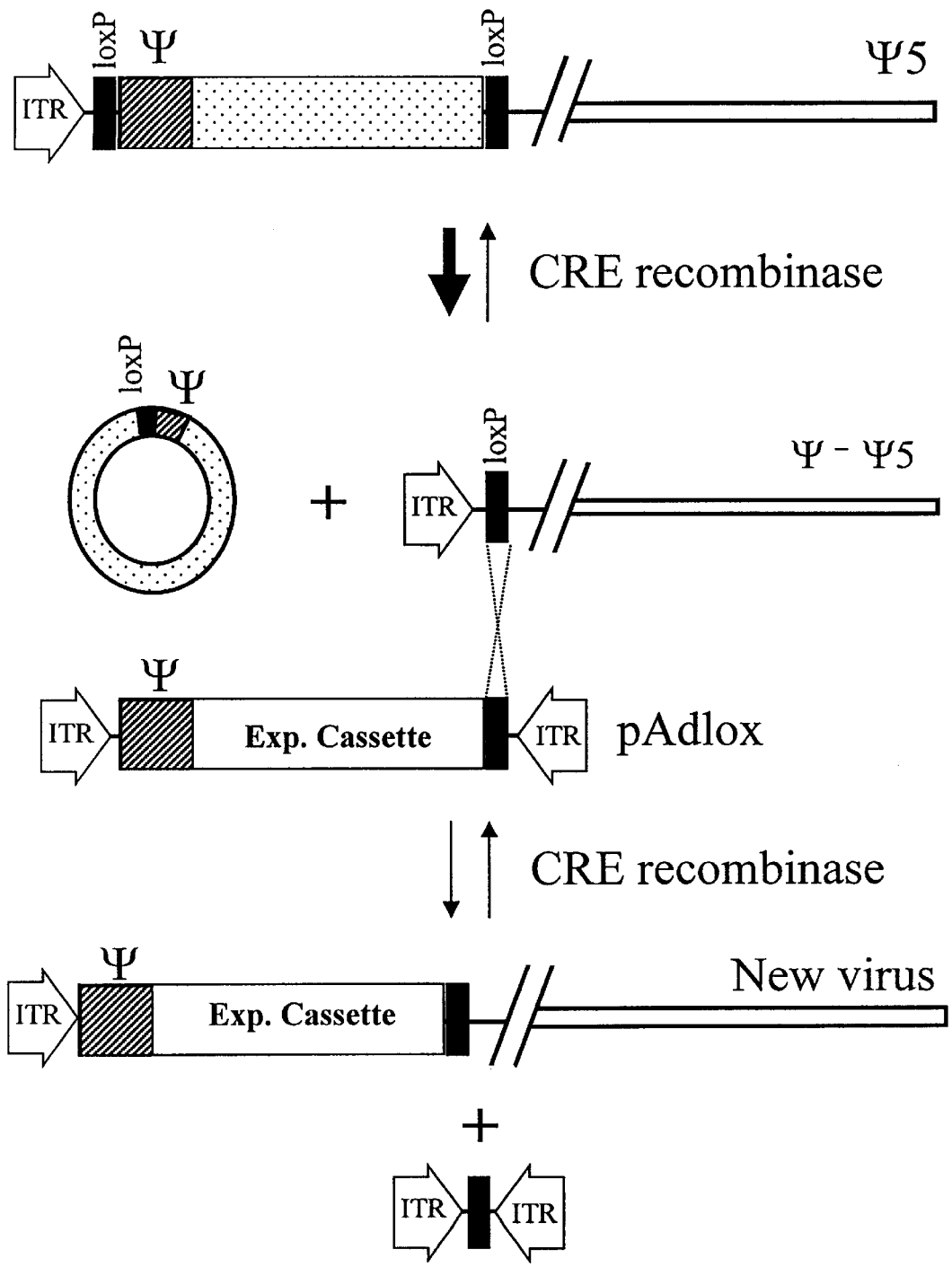

FIG. 14. Construction of an E1-substituted adenovirus by using ψ5 and a replicating vector. Negative pressure on ψ5 is achieved by intramolecular recombination removing the packaging site in the first step. An intermolecular recombination between the replicating vector and ψ5 then creates a new virus which has an intact packaging site and carries a recombinant gene, marked Exp. Cassette. The packaging site is labeled ψ.

DESCRIPTION OF SPECIFIC EMBODIMENTS

The present invention provides an integrated system for the in vivo production of substantially pure preparations of packaged adenovirus-based vectors useful for gene therapy and gene transfer and expression in mammalian cells. The system has several components including a therapeutic recombinant adenovirus vector, a helper recombinant adenovirus vector and a host cell line which expresses Cre recombinase. The present invention provides each of these components individually as well as a method for production of in vivo packaged therapeutic rAd vectors using the system.

In brief, the method of the present invention works as follows. A eukaryotic host cell which is susceptible to adenovirus infection is transfected with a therapeutic rAd vector and a helper rAd vector. The therapeutic rAd vector is replicated and packaged in the transfected host by the replication and packaging system that is supplied by the helper virus. The therapeutic rAd vector contains Ad DNA sequences only from the ITRs and the packaging site, the remainder of the DNA in the therapeutic rAd vector is from non-adenovirus sources. The helper rAd vector is constructed so that the packaging site is flanked by lox sites which recombine with great efficiency in the presence of Cre recombinase. The recombination of the lox sites results in the excision of the packaging site. The efficiency of the excision of the packaging site in the helper can be improved by using more than one set of lox sites flanking the packaging site. The system contains the further safeguard that any homologous recombination between the helper rAd vector and the therapeutic rAd vector (whether Cre-mediated or not) can only result in a helper rAd vector in which the packaging site is still flanked by lox sites and thus still vulnerable to excision. The transfection produces a mixture of packaged particles, both therapeutic rAd vector particles and helper rAd vector particles. The packaged viral particles from the transfection are isolated by standard methods and used to infect additional host cells. The infection steps may be repeated a number of times until the titer of the viral particles is produced in sufficient quantities. In the final infection step, host cells capable of expressing the Cre recombinase are used. Cre-expressing host cells may be used in all of the transfection and infection steps as well, however, for infection and transfection steps other than the final one, non-Cre expressing cells are preferred because of the possibility that prolonged selective pressure will result in unwanted deletions in the helper rAd vector.

Figure 1:
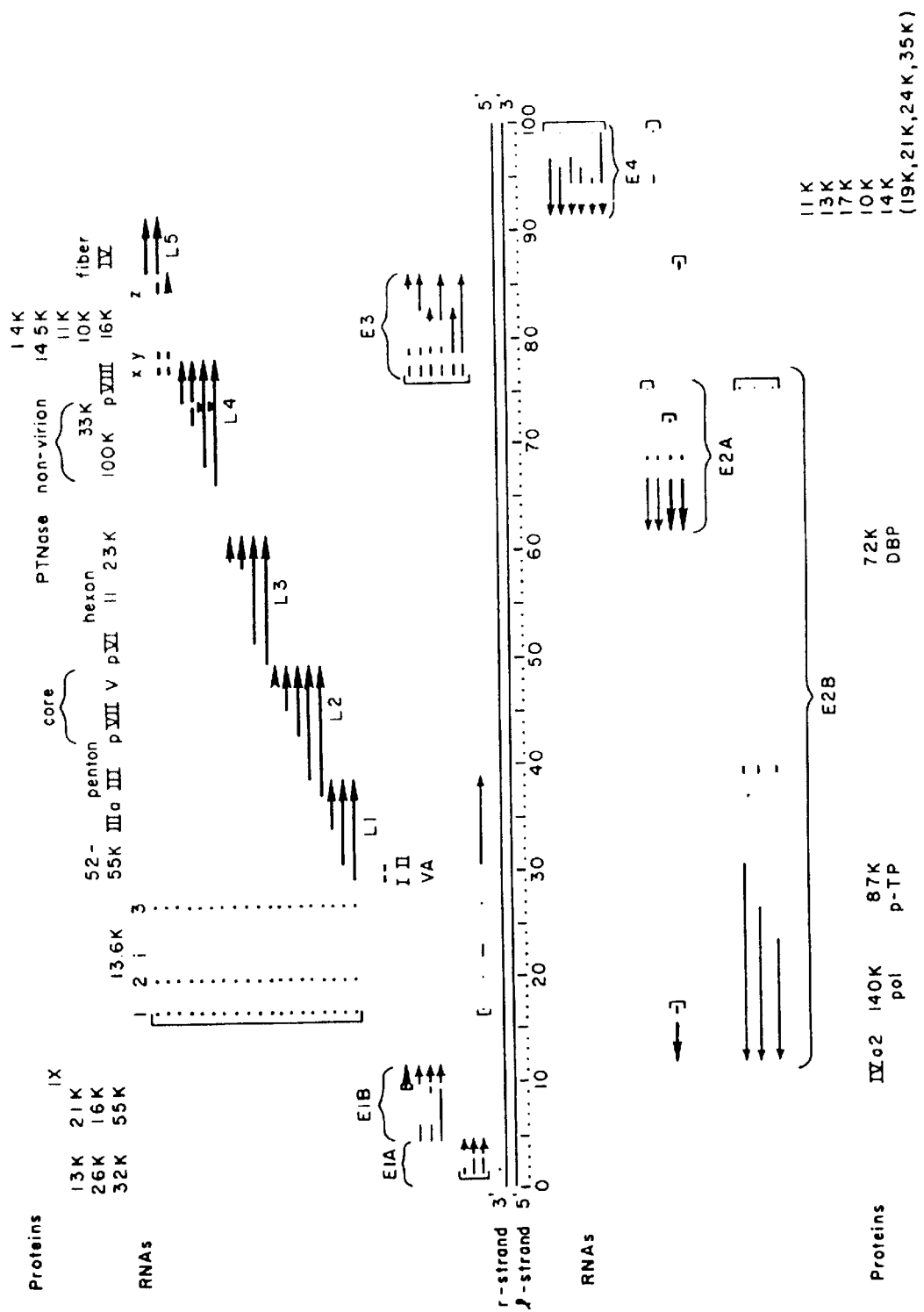
FIG. 1. The genetic map of a wild type Adenovirus. (DNA Tumor Viruses: Control of Gene Expression and Replication 1986; Editors: Michael Botchan, Terri Grodzicker, and Phillip A. Sharp; pages 37-57.)

For ease of description of the rAd vectors of the present invention, reference will be made to the genetic map of adenovirus in FIG. 1. The terms "left" and "right" are defined with reference to the structure of adenovirus as it appears in FIG. 1. The terms "3'" and "5'" are defined with reference to the upper DNA strand as shown in FIG. 1. The rAd vectors of the present invention, including the therapeutic rAd vector and the helper rAd vector, while different in some respects from the wild type adenovirus genetic map in FIG. 1, still retain certain adenovirus structural landmarks (e.g. ITRs, packaging site) so that the left/right designation retains the same meaning for the rAd vectors as for wild type Ad. The complete sequence of the wild type Ad5 virus is known and can be found in Chroboczek et al. Virology 186:280–285 (1992), GENBANK Accession No. M73260.

The therapeutic rAd vectors of the present invention comprise DNA molecules containing adenovirus inverted terminal repeats (ITRs), an adenovirus packaging site and one or more lox sites. The therapeutic rAd vectors additionally comprise a foreign DNA sequence of interest. The ITRs and the packaging site are required in cis for replication and packaging of the therapeutic vectors in vivo. Adenovirus ITRs useful for the therapeutic rAd vectors of the present invention can be the ITRs from any adenovirus as long as they are recognized by the replication and packaging proteins supplied in trans by the helper rAd vector. All naturally occurring adenoviruses have inverted terminal repeats although the length and sequence of the ITRs vary among different adenovirus serotypes. The sequences of many of the ITRs are known (see for example, Sussenbach, J. in "The Adenoviruses" pages 35–113 Ginsberg, H. ed. Plenum Press 1984). Preferably, the ITRs in the therapeutic rAd vectors are the ITRs from Ad2, Ad3, Ad4, Ad5, Ad7, Ad9, Ad10, Ad12, Ad18 or Ad31. More preferably the ITRs are from Ad5. The ITRs are oriented in the therapeutic rAd vectors in the same manner in which they are oriented in the naturally occurring adenovirus, that is, the sequences are inverted with respect to one another and occur at the terminals of the therapeutic rAd vectors. In the therapeutic rAd vectors, the ITRs are separated by the lox site or sites, the packaging site, and the foreign DNA sequence of interest.

The adenovirus packaging site is required in cis for packaging of the DNA into the adenovirus virions. All adenovirus strains analyzed to date contain a packaging site, typically located at the left end of the viral genome, adjacent to and to the right of the left ITR. In addition to the naturally-occurring Ad packaging sites, certain other DNA sequences have been shown empirically to function as packaging sites. Such sequences are referred to as synthetic packaging sites. For the therapeutic rAd vectors of the present invention, any naturally-occurring or synthetic adenovirus packaging site is suitable as long as the site is recognized by the packaging system of the helper rAd virus used. Preferably, the packaging site is that from Ad5. In particular, the Ad5 packaging site is the DNA sequence from base pair 194 to base pair 452 of the Ad5 genome as measured from the left end. More preferably, the packaging site is the DNA sequence from base pair 194 to base pair 375 of the Ad5 genome as measured from the left end. Alternatively, the packaging site useful for the therapeutic rAd vectors of the present invention may be a synthetic packaging site. For example, one synthetic packaging site composed of six tandemly repeated copies of the "A" repeat has been shown the function as a packaging site in vivo (Grable and Hearing J. Virol. 64:2047–2056). Preferably, for the therapeutic rAd vectors of the present invention, the packaging site is a naturally-occurring adenovirus packaging site.

The therapeutic rAd vectors of the present invention contain at least one lox site for recombination. Lox sites are the sites at which Cre-mediated recombination occurs. The presence of at least one lox site in the therapeutic rAd vector of the same type as at least one of the lox sites in the helper rAd vector serves to insure that any homologous recombination between the therapeutic rAd vector and the helper rAd vector (through the ITRs or packaging sites, for example) can only result in helper rAd vectors which still retain lox sites flanking the packaging site. Several types of lox sites have been identified and their sequences are well known. Any lox site that is capable of undergoing Cre-mediated recombination is suitable for use in the therapeutic rAd vector. Preferably for the therapeutic rAd vectors of the present invention, one or more of the following lox sites are useful: lox P, lox 511, lox 514 and lox Psym (Hoess et al. Nucl. Acids Res. 14:2287–2301 1986). The sequence of several lox sites are shown in FIG. 2. The therapeutic rAd vectors of the present invention may contain one or more types of lox sites but will contain no more than one lox site of each type. At least one of the lox site(s) used in the therapeutic rAD vector will be of the same type as at least one of the lox sites used in the helper rAd vector as described below.

The therapeutic rAd vectors of the present invention contain a foreign DNA sequence of interest. The foreign DNA sequence of interest typically comprises genes or other DNA sequences that are of interest to transfer into mammalian cells. Foreign DNA sequence of interest may include any naturally occurring or synthetic DNA sequence. The foreign DNA may encode protein, or contain regulatory sites, including but not limited to, transcription factor binding sites, promoters, enhancers, silencers, ribosome binding sequences, recombination sites, origins of replication, sequences which regulate RNA stability and polyadenylation signals. The foreign DNA may be identical in sequence to naturally-occurring DNA or may be mutated relative to the naturally occurring sequence. The foreign DNA need not be characterized as to sequence or function.

The size of foreign DNA that may be included in the therapeutic rAd vector will depend upon the size of the rest of the vector. Preferably, the total size of foreign DNA is from 36 kb to 37.4 kb. The total size of the therapeutic rAd vector will be not larger than about 38 kb. Preferably, the total size of the therapeutic rAd vector is from 32 to 38 kb; more preferably, from 34 kb to 37 kb; and most preferably from 35 kb to 36 kb. The lower size limit for packaging efficiency (i.e. at least 80% of wild type packaging efficiency) is around 32 kb total rAd vector. Recombinant Ad viruses that are smaller than 32 kb are not as stable, which can create significant problems for reliable delivery of the same recombinant vector for gene therapy. This discovery of the optimum packaging size is also important for manufacturing large quantities of the viral particles for commercial use, in which case packaging efficiencies on the order of wild type efficiencies are desired.

The construction of the therapeutic rAd vector of the present invention is accomplished by operationally joining the various required DNA sequences that comprise the therapeutic rAd vector, that is, the left and right ITR sequences, the adenovirus packaging site sequence, the lox site sequence(s) and the foreign DNA sequence of interest. The various required DNA sequences are joined together in a particular order and in a specific orientation with regard to one another. The order and orientation of the sequences is illustrated from the left to right direction as follows: a left inverted terminal repeat, one or more lox recombination sites, an adenovirus packaging site, a foreign DNA sequence of interest, a right inverted terminal repeat. The required sequences may be joined directly to one another or additional DNA sequences may intervene between the required sequences. The additional intervening DNA sequences may be residual from the cloning process used to join the required sequences or may be particular sequences positioned between or within the required DNA sequences in order to aid in manipulation or efficiency of the vectors, for example, restriction sites, PCR priming sites, promoters, selectable marker genes and the like. The left and right inverted terminal repeats are oriented toward one another in the therapeutic rAd vector in the same manner as that in which they are found naturally-occurring in the adenovirus, that is they are inversely oriented with respect to one another. By inversely oriented is meant that when read on the same strand in the 5' to 3' direction, the ITR sequences are the reverse complements of one another. The orientation of the packaging site is not critical for the vectors of the present invention so that the packaging site may be oriented in either direction with respect to the left ITR. The packaging site will be positioned no more than 400 bp from the left end of the therapeutic rAd vector, preferably no more than 300 bp from the left end of the vector. The lox site is oriented with respect to the packaging site in the same manner as are the identical lox sites in the helper rAd with respect to the packaging site, as described below. If more than one type of lox site is present, the lox sites may preferably be ordered in the same manner as they occur on the left side of the packaging site in the particular helper rAd vector to be used with the therapeutic rAd vector. The foreign DNA of interest may be oriented in any appropriate orientation with respect to the rest of the vector. The sequences are joined together by any of a number of techniques that are well known in the DNA cloning art. The joining is most conveniently accomplished by ligation of DNA fragments, for instance restriction fragments or chemically or enzymatically synthesized DNA fragments, containing the various required DNA sequences. Alternatively, the various required DNA sequences may be chemically or enzymatically synthesized as a single DNA fragment or two or more of the various required sequences may be synthesized as a single fragment and joined to the remaining sequences.

As an alternative to in vitro vector construction methods described above, the therapeutic rAd may be constructed in vivo by homologous recombination techniques that are well known in the art (see for example, Chinniduri et al. J. Virol. 32:623–628 (1979); Bett et al. (1994)). In vivo construction using Cre-mediated recombination of lox sites may also be used to create the therapeutic rAd vector. For this purpose, a precursor therapeutic rAd vector may be constructed without ITR sequences and containing an additional lox site, located at the right-most end of the foreign DNA. The precursor therapeutic rAd vector thus has the following sequences in order: a first lox site, an Ad packaging site, the foreign DNA, and a second lox site not identical to the first site. A modified helper rAd vector is constructed as described below except that an additional lox site, identical to the second lox site in the precursor therapeutic rAd vector, is positioned adjacent to and to the left of the right ITR. The additional lox site is not identical to any of the other lox sites in the modified helper. The precursor therapeutic rAd vector and the modified helper rAd are transfected into a Cre-expressing host cell and Cre-mediated recombination results in a transfer of the ITRs from the modified helper to the precursor therapeutic rAd to form a therapeutic rAd vector.

The therapeutic rAd vector may be conveniently cloned into a prokaryotic cloning vehicle (for example, plasmids, bacteriophages, phagemids, etc.) for easy propagation in a bacterial host. Alternatively, a eukaryotic cloning vehicle may be used. For this purpose, restriction sites may be added to the outer most ends of the ITRs. Prior to use for transfection, the therapeutic rAd vector is removed from the cloning vehicle by appropriate restriction digestion. It will be apparent that the therapeutic rAd vector may be constructed first and then cloned into a cloning vehicle or each sequence required in the therapeutic rAd vector may be added separately to the cloning vehicle. Methods of vector construction are well known in the art and one of ordinary skill would readily be able to determine an appropriate cloning strategy for construction of the therapeutic rAd of the present invention either with or without a cloning vehicle.

The helper rAd vector of the present invention comprises a DNA molecule containing adenovirus genes which encode proteins necessary for the replication and packaging of the therapeutic rAd vectors into therapeutic rAd virus particles. The helper rAd vector of the present invention additionally comprises an adenovirus packaging site, flanked by at least one set of two identical lox sites in direct orientation with respect to one another, and a left and a right ITR. The helper rAd vector may contain an entire adenovirus genome provided that any packaging site is flanked by at least one set of two directly-oriented, identical lox sites. Particular adenovirus genes may be omitted from the helper rAd virus if the products of the omitted genes are not essential for the replication and packaging of the therapeutic rAd (for example, the E3 proteins, E4 or 1–4 or VAII) or can be supplied otherwise than from the helper rAd vector, for example, from the host cell. The determination of which Ad genes may be omitted from the helper rAd is well within the ability of one of ordinary skill in the art. Preferably, the helper rAd vector will contain the entire adenovirus genome except for the E1a and E1b regions. When the helper rAd vector does not contain the E1a and E1b regions, it is preferably used in combination with a host cell in which the E1a and E1b gene products are supplied from the host. The E1a and E1b gene products are preferably transcribed from heterologous promoters in the host cell.

The adenovirus packaging site suitable for the helper rAd vector of the present invention includes any of the packaging sites that are useful for the therapeutic rAd vector. Preferably, a synthetic packaging site is useful for the helper rAd vector. In general, Ad vectors containing the synthetic packaging sites are less efficiently packaged. Use of such a site therefore contributes to the selection against the helper rAd. Most preferably, the packaging site comprises a DNA sequence of six tandemly repeated "A" repeats (Grable and Hearing, J. Virol. 64:2047–2056).

The packaging site of the helper rAd vector is flanked by at least one set of two identical lox sites in direct orientation with respect to one another, one of the set being on the left (5'-most) side of the packaging site and one of the set being on the right (3'-most) side of the packaging site. By direct orientation is meant that the sequences of the lox sites when read in the 5' to 3' direction on the same DNA strand are identical. When more than one set of two identical lox sites is present in the helper rAd vector they will be arranged so as to form a nested set; that is, one member of each set will be positioned on the left side of the packaging site and one member will be positioned on the right side of the packaging site and the order of the sites as they occur on the right side of the packaging site will be opposite to that in which they occur on the left side but the two identical members of each set will be in the direct orientation with respect to one another.

One such nested set may be illustrated by a simple example. A helper rAd having three sets of two identical lox sites, for instance one set each of lox P, lox 511 and lox 514, may be arranged in order . . . lox P(→)-lox 511(→)-lox 514(→)-packaging site-lox 514(→)-lox 511(→)-lox P(→) . . . where the arrows indicate the directionality of the lox sites.

Where more than one set of two identical lox sites are used, the identical innermost lox sites will preferably be separated from one another by at least 60 base pairs of spacer DNA, wherein the identical lox sites are in phase with each other (i.e. the distance between the identical lox sites before the recombinase/excision step is a multiple of 10.5 base pairs). The lox sites should also be preferably at least 14 bases apart from the adjacent, non-identical lox sites. The distances between lox sites can be created by addition of spacer DNA. The addition of spacer DNA between the lox sites insures that there will be a sufficient amount of intervening DNA between the remaining identical lox sites for recombination to occur after recombination has occurred between the innermost lox sites in the nested set. The center-to-center distance between the innermost nested lox sites will contain the packaging site, which is greater than the minimal size between lox sites that is required for excision by recombinase—roughly 60 base pairs. The center-to-center distance between the innermost lox sites preferably will be the sum of the size of the packaging site plus additional spacer DNA such that the sum is a multiple of 10.5. The center-to-center distance being a multiple of 10.5 base pairs in length places the lox sites in phase with each other, since there are roughly 10.5 bases per helical turn. The second set of nested lox sites, flanking the innermost set, should comprise two different lox sites, each preferably at least 14 bases distant from the center of the adjacent, non-identical innermost lox site. The distance between the second set of nested lox sites and the adjacent, non-identical innermost lox sites can be optimized by calculating a distance between the second set of nested lox sites that is a multiple of 10.5 bases pairs after excision of the innermost lox sites, wherein the excision leaves a single innermost lox site and spacer DNA. The phasing of lox sites can also be calculated in designing the third set of flanking lox sites in a nested set lox site configuration.

The spacer DNA inserted between the lox sites may also enhance the Cre mediated recombination. In general, it appears that the spacer sequence may be nonspecific and only its length of importance. For instance, interaction between proteins at two different sites on DNA is maximal when the proteins are in phase, that is on the same face of the DNA helix. There are about 10 base pairs per turn of the DNA helix. Additionally, since the helper virus DNA may be in nucleosomes the phasing of the sites for maximal recombination may reflect nucleosomal phasing of 160 to 200 base pairs. However, some aspects of the sequence in the spacer may also be important. As is well known in the art, certain sequences bend DNA or alter its stiffness. In addition, DNA binding proteins can bend DNA and some DNA binding proteins can displace or phase nucleosomes. The spacer DNA may separate the lox sites on the right side of the packaging site or those on the left side of the packaging site or both. Preferably, the spacer DNA will separate the lox sites on the right side of the packaging site. As in the therapeutic rAd vector, the packaging site in the helper rAd vector will be no more than 400 base pairs, preferably no more than 300 base pairs, from the left ITR.

The left and right ITRs useful for the helper rAd vector can be the ITRs from any adenovirus as long as they are recognized by replication and packaging proteins expressed by the helper rAd vector. Preferably, the ITRs in the helper rAd vectors are the ITRs from Ad2, Ad3, Ad4, Ad5, Ad7, Ad9, Ad10, Ad12, Ad18 or Ad31. More preferably the ITRs are from Ad5. The ITRs are oriented in the helper rAd vectors in the same manner in which they are oriented in the naturally occurring adenovirus, that is, the sequences are inverted with respect to one another and occur at the terminals of the helper rAd vectors. In the helper rAd vectors, the ITRs are separated by the packaging site, which itself is flanked by at least one identical set of lox sites, and adenoviral DNA which encodes the proteins necessary for replication and packaging.

The helper rAd vector may be constructed using any of a number of cloning techniques well known in the art. Such techniques have been described for the construction of the therapeutic rAd vector and include in vitro cloning, in vivo recombination, chemical or enzymatic synthesis, and any other appropriate methods.

A Cre-expressing host cell culture for use in the present invention can be made in any of a number of ways that are well known in the art. The Cre expressing host cell may be made by transfection of a mammalian cell culture that is susceptible to infection by adenovirus with a DNA vector containing a functional Cre gene or coding sequence. By functional is meant that the gene or coding sequence also contains those regulatory sequences necessary for transcription, translation and localization in the cell into which it is delivered such that Cre is expressed. For example, Adenovirus susceptible cells may be transfected with a vector carrying the Cre gene from bacteriophage P1, under control of a eukaryotic promoter, for example the immediate-early promoter of CMV. The bacteriophage Cre gene may be modified, using techniques that are well known in the art, to include a Kozak sequence and a nuclear localization signal for maximum translational efficiency and transport into the nucleus. Transfectants may be assayed for Cre activity by any conventional method including Western blots with Cre-specific antibody or functional assays for protein activity (see, for example, Adams et al. J. Mol. Biol. 226:661–673). Typically, for use in the present invention, Cre-expressing host cell culture will produce an intracellular Cre concentration of between 0.1 $\mu$M and 50 $\mu$M, preferably between 1 $\mu$M and 20 $\mu$M. Preferably, the Cre-expressing host cell culture will also express E1a and E1b and the cell will not contain the adenovirus packaging site. In addition, the chromosomal or episomal DNA of the Cre-expressing host cell preferably does not contain any sequences capable of recombination with the helper rAd vector.

The method of the present invention provides for the production of a substantially pure preparation of packaged therapeutic rAd vector particles. By a packaged therapeutic rAd vector particle is meant a therapeutic rAd vector DNA packaged into an adenovirus virion to form an infectious particle. The packaged therapeutic rAd vector particles may also be referred to as therapeutic rAd virus. By infectious is meant that the packaged particle is at least capable of binding to the high affinity Ad receptor on the host cell, followed by internalization and transport of the DNA to the nucleus. By substantially pure is meant a preparation in which at least 95% of the vector particles present are therapeutic rAd vector particles; preferably at least 99% of the vector particles present are therapeutic rAd vector particles, more preferably at least 99.5% of the vector particles present are therapeutic rAd vector particles.

The method of the present invention is initiated by transfecting a host cell susceptible to adenovirus infection with a therapeutic rAd vector and a helper rAd vector. The host cell preferably does not contain any chromosomal or episomal DNA which is capable of recombination with the helper rAd vector. The host cell used for transfection may be any cell culture susceptible to Adenovirus infection. The host may be one which is capable of expressing Cre recombinase, but non-Cre-expressing host cells are preferred for the transfection step. The choice of a particular therapeutic rAd vector and a particular helper rAd vector is limited only by two requirements: (1) that the replication and packaging proteins encoded by the helper rAd vector must be able to recognize the ITRs of the helper rAd vector and the ITRs and packaging site of the therapeutic rAd vector and (2) that the therapeutic rAd vector must contain at least one lox site to the left of the packaging site that is identical to one of the lox sites in the equivalent position in the helper rAd vector. If the rAd vectors have been cloned into and propagated in cloning vehicles, the cloning vehicle DNA may be removed prior to transfection such that only the rAd vector is used. The cloning vehicle DNA may be removed in any of a number of ways that are well known in the art, for example by restriction digestion or by synthesis of PCR fragments containing only the rAd vector sequences.

Transfection may be performed by the DEAE-dextran method (McCutchen and Pagano, 1968, J. Natl. Cancer Inst. 41:351–357), the calcium phosphate procedure (Graham et al., J. Virol. 33:739–748 (1973); Graham and van der Eb, Virology 52:456–467 (1973)) or by any other method known in the art, including but not limited to microinjection, lipofection, and electroporation. In most cases, the cells will be transfected with the helper rAd and the therapeutic rAd simultaneously, although there may be instances in which it is more appropriate to transfect with each vector separately. Typically, an equimolar amount of the helper rAd vector and the therapeutic rAd vector will be used but this may be varied for optimal yields depending on the vectors used. Determination of the appropriate ratio for transfection is well within the skill of one of ordinary skill in the art.

The transfected cells are cultured in a suitable medium, for example DMEM, for a time sufficient to provide for maximum replication and packaging of the therapeutic rAd vectors into viral particles. The point of maximum replication and packaging of the therapeutic rAd can be estimated by determining the viral yield at various times after transfection. The viral yield can be determined by conventional methods, including infection of Ad susceptible host with lysates and counting the number of infected cells expressing a marker gene contained in the foreign DNA, quantitative PCR for sequences unique to the therapeutic rAd, measurement of absorbance of the viral preparation at 280 nm after correcting for any helper virus that might be present (the titer of any contaminating helper rAd virus is easily determined by plaque assays), or by measurement of absorbance of the viral DNA at 260 nm (any contamination with helper rAd DNA can be determined by appropriate restriction digestion). In most cases, 72 hours is a sufficient time period for culturing the transfected cells. Following the transfection and during the culturing period, the helper rAd is transcribed and translated to produce the adenovirus gene products necessary for the replication and packaging of the therapeutic rAd.

The packaged vector particles are isolated from the transfected cells by conventional means. Conventional means includes producing a lysate of the whole plate or overlaying the monolayer of cells with agar and then removing only the infected cells in the plaques. Plaques are made of dead infected cells and are visible to the eye. The plaques may also be stained for expression of a marker gene in the rAd virus. Plaque isolation is typically done at about a week after transfection. The vector particles isolated from the transfected cells are a mixture of packaged therapeutic rAd vector particles and packaged helper rAd vector particles. The mixture of vector particles isolated from the transfected cells is used to infect a fresh host cell culture by methods that are well known in the art. Packaged viral particles are isolated from the infected cells and the infection process is repeated with fresh host cells in order to amplify the viral titer with each passage. Since the yield of rAd virus from the transfection is quite small, it is important to infect a small number of cells ($10^2$). At each passage the cell number is increased $10^2$ to $10^4$ to $10^6$ to $10^8$. Because infection with the packaged vector particles is much more efficient than transfection with the naked vector DNA, more of the cells will receive and replicate the vectors in the infection steps.

As in the transfection, the co-infection yields a mixture of packaged rAd particles. The packaged rAd vector particles are isolated from the infected cells in the same manner as from the transfected cells and may be used to repeat the infection steps as many times as necessary to produce a sufficient titer of substantially pure packaged therapeutic rAd vector particles. In general the titer will be between $10^7$ and $10^{10}$ per ml, preferably between $10^9$ and $10^{10}$ per ml.

In the final step of the method of the present invention, a Cre-expressing cell line is used as the host cell for infection. In the Cre-expressing cells, the helper rAd undergoes replication but the packaging of the helper rAd will be limited because Cre-mediated recombination between the lox sites will result in the excision of the packaging site from a large percentage of the helper rAd molecules. Helper rAd without the packaging site is not packaged into virions. When one set of lox sites is present in the helper rAd, packaging site will be excised in about 95% of the molecules; when two sets of lox sites are used, the molecules with an excised packaging site increases to about 99%; when three sets are used the percentage increases to about 99.99%. In addition, any host-mediated recombination that may occur between the therapeutic rAd vector and the helper rAd vector (for example, due to the possible homology of the ITRs or the packaging sites) during the replication and packaging process will not result in regeneration of a wild type adenovirus. Because the therapeutic rAd vector contains a lox site between the left ITR and the packaging site, any recombination with the helper rAd will result only in a helper vector in which the packaging site is still flanked by at least one set of identical lox sites as long as the lox site in the therapeutic virus is identical to at least one of the lox sites in the helper rAd vector.

Typically the method of the present invention is carried out as follows. The therapeutic rAd vector and the helper rAd vector are transfected into non-Cre-expressing cells (that is, non-selective cells). The monolayer of transfected cells is overlain with agar and plaques are removed after one week. The virus mixture from the plaques is passed successively by infection onto increasing numbers of non-Cre-expressing (non-selective) cells; $10^7$ non-Cre-expressing cells are infected and the resulting viral DNA is screened for the presence of the rAd virus. The helper virus is reduced in the final passage by infecting Cre recombinase expressing cells. By limiting passage of the helper rAd through Cre-expressing host cells to the final infection step, helper virus is not under continuous selection and the possibility of mutations rendering the helper resistant to Cre selection is lessened.

In another embodiment, the present invention comprises a method for rapidly and efficiently generating new recombinant adenovirus vectors with substitutions in the E1 region or any other adenoviral region. This method uses a helper rAd of the present invention, for example ψ5, and Cre-expressing host cells to generate new adenovirus recombinants in vivo. The helper vector comprises a packaging site flanked by recombination sites and an ITR, wherein the packaging site can be located at either end of the helper vector. The helper vector can also contain adenoviral or foreign DNA sequences between the recombination sites, wherein the adenoviral or foreign DNA sequences can be excised or deleted via recombinase-mediated recombination. The adenoviral DNA to be deleted can be from any region of the adenoviral genome expressing genes that can be complemented. One advantage of deleting adenoviral or foreign DNA sequences is to provide room for substitute DNA. The helper rAd vector is transfected or infected into Cre-expressing host cells along with a replicating vector containing the Ad ITRs separated by an Ad packaging site, the substitute DNA to be substituted into the E1 region (or any region in which a substitution is preferred) and a lox site identical to at least one of the lox sites in the helper rAd vector. During the growth of the virus in the transfected cells, the packaging site in the helper rAd is excised by Cre-mediated recombination to yield a deleted helper rAd (Δ-helper) containing no packaging site and only a single lox site. Recombination of the Δ-helper with the replicating vector at the lox site yields packageable virus containing the essential viral genes from the Δ-helper and the substitute DNA from the replicating vector. If the substitute DNA includes adenoviral genes that are necessary for replication, then the resulting substituted rAd vector will be a replicating virus. On the other hand, if the substitute DNA does not introduce adenoviral genes that are necessary for replication and are not otherwise available, then the resulting substituted rAd vector will be a nonreplicating virus.

One of ordinary skill in the art will appreciate that this method can be used to generate new rAd vectors with substitutions in any Ad region, including but not limited to the E1 region.

By replicating vector is meant any vector that can be replicated by the adenovirus replication system. The replicating vector must contain Ad inverted terminal repeats. The replicating vector will also contain an Ad packaging site and a lox site. Preferably the replicating vector will additionally contain substitute DNA inserted between the packaging site and the lox site. The replicating vector is preferably pAdlox or pAdlox derivatives having the substitute DNA inserted in the polylinker region. By substitute DNA is meant any DNA to be substituted into the E1 or other Ad region.

By using selection against ψ5, a recombinant adenovirus carrying substitute DNA in place of the E1 genes was generated by cotransfecting a replicating vector with a loxP site (pAdlox) and ψ5 DNA into a CRE8 cells (FIG. 14). In the first step of the reaction, Cre recombinase catalyzes recombination between the two loxP sites in ψ5, removing the packaging site from the virus. In the second step, Cre recombinase catalyzes a recombination between ψ5 and pAdlox, transferring the substitute DNA into ψ5. The resulting recombinant virus will now have a single loxP site and therefore will have a considerable growth advantage over ψ5 in CRE8 cells. This growth advantage should generate virus stocks comprised predominantly of the recombinant adenovirus having a substitution.

Specific examples of the steps described above are set forth in the following examples. However, it will be apparent to one of ordinary skill in the art that many modifications are possible and that the examples are provided for purposes of illustration only and are not limiting of the invention unless so specified.

EXAMPLES

Example 1

Construction of the ψ5 Helper rAd Vector

The starting material for construction of the helper rAd vector ψ5 was a plasmid containing the following sequences in order: an SfiI restriction site, nucleotides 2 to 553 from Ad5 (nucleotide 1 is the last C of the SfiI site), an XhoI restriction site, the human CMV immediate-early promoter from −600 to +1 relative to the start of transcription, the polylinker sequence from pSP73 from the HindIII site to the EcoRI site, a polyadenylation signal from SV40 (nucleotides 2752 to 2534 of SV40), pSP73 sequence from nucleotide 2 through 2382 (containing ClaI, EcoRV, and BglII sites), an ApaI restriction site, the right ITR from Ad5. The ApaI-SfiI fragment containing the right ITR was made by polymerase chain reaction. For ease of manipulation the SfiI fragment was cloned into the PvuII site of pBluescript+ to give pCMV-Ad. Cleavage of pCMV-Ad with SfiI releases the original SfiI fragment.

Figure 3:
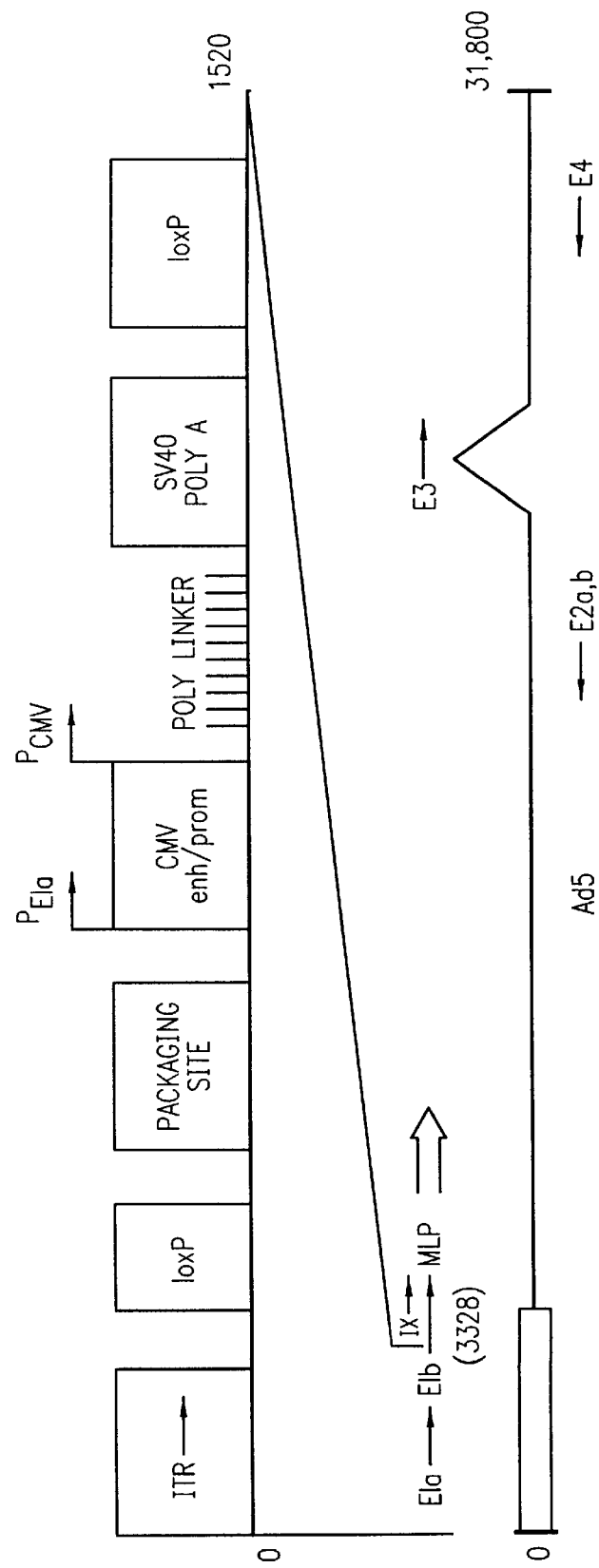
FIG. 3. Schematic representation of the helper rAd helper vector ψ5. The bottom figure represents the complete ψ5 genome. The upper figure shows the details of the structure of the insert carrying the packaging site flanked by the lox P sites which is substituted into the Ad5 at position 0-3328.

Next, a single lox P site (chemically synthesized) was inserted into pCMV-Ad between the ClaI and BglII sites to give plasmid pAdlox. A second lox P site was inserted into pAdlox between nucleotides 193 and 194 of the Ad5 left end fragment to give pfloxPac. The orientation of the two lox P sites in pfloxPac is the same. Finally, nucleotides 3328 through 8914 of Ad5 were inserted into the BglII site of pfloxPac to create pfloxPacB.

ψ5 was made by overlap recombination between SfiI cleaved pfloxPacB and ClaI cleaved Adβgal in 293 cells using $CaPO_4$ transfection (Chinniduri et al. J. Virol. 32:623–628(1979)). Adβgal contains wild type adenovirus sequence from nucleotide 3328 through the right end except for a deletion between nucleotides 28,592 and 30,470 in the E3 region. The resulting recombinant virus was isolated by plaque purification using standard techniques. The structure of ψ5 is shown in FIG. 3.

Example 2

Construction of a Therapeutic rAd Vector Minus Lox Site

A minimal rAd vector was constructed containing the ITRs, Ad packaging site and about 27 kb of foreign DNA. This prototype therapeutic rAd vector did not contain a lox site.

The starting material was pCMV Ad described in Example 1. The 22 kb BglII A fragment from λ phage DNA was inserted between the BamHI and the BglII sites of pCMV Ad. A 5 kb BamHI DNA fragment containing a CMV immediate early promoter, the β-galactosidase gene and SV40 polyadenylation signal was also inserted into the BglII site. The resulting plasmid, pAβ, contains a 28 kb DNA fragment, including an Ad packaging site, bounded by two ITRs. The ITR bounded fragment can be excised by SfiI digestion.

To determine whether this vector would be replicated and packaged in vivo with a helper virus, pAβ treated in various ways was co-transfected with Adenovirus DNA into 293 cells. The treatments were as follows: 1) pAβ transfected as circular plasmid, 2) pAβ was digested with PstI before transfection (PstI digestion excises the β-gal expression cassette from the ITRs and the packaging site), 3) pAβ was digested with SfiI before transfection (SfiI digestion excises the entire ITR bounded fragment). Three μg of treated plasmid and 3 μg of adenovirus DNA were transfected into 293 cells by $CaPO_4$ precipitation. As a control, 3 μg of a β-galactosidase expressing plasmid was co-transfected with 3 μg Adenovirus DNA. Three days after transfection, virus was harvested by three cycles of freeze-thawing and 0.2 ml of each lysate was used to infect 293 cells. The infected cells were scored for β-galactosidase activity. The results were as follows: 1) uncut pAβ, 100/ml; 2) PstI cut pAβ, 200/ml; 3) SfiI cut pAβ, 2000/ml; 4) control β-galactosidase expression plasmid, 100/ml.

Example 3

Isolation of Cre8 Cre-expressing Host Cell Line

To make a stable cell line expressing Cre recombinase, 293 cells were transfected with plasmid pML78 using the $CaPO_4$ precipitation method (Graham et al. Virology 52:456–467 (1973)). pML78 contains the Cre recombinase gene, modified to include a Kozak sequence at the start of translation and a nuclear localization signal at the N-terminal, under the control of a human β-actin promoter and followed by the poly A signal from β-actin. pML78 also contains a selectable neomycin resistance gene.

At 48 hr. after transfection, the cells were transferred into culture medium containing G418. After selection on G418 for 17 days, 12 resistant colonies were recovered and expanded.

As a first step in characterization of the transfectants, Western blot analysis was performed on cell extracts. A 10 cm dish of cells (about $1.6 \times 10^7$ cells) was washed once with phosphate buffered saline (PBS) and the cells were suspended in 5 ml PBS and centrifuged for 1 min. The cell pellet was resuspended in 400 μl extraction buffer (50 mM Tris-HCl, pH 7.5, 150 mM NaCl, 1 mM EDTA, 1.25% Triton X-100, 0.5 mM PMSF) and the cells were lysed by passing through a pipet tip 20 times. The lysate was gently mixed at 4° C. for 30 min. and cleared by centrifugation for 3 min. in a microfuge at 4° C. The protein concentration of each extract was measured and an aliquot containing 200 μg protein was electrophoretically separated on a 10% polyacrylamide gel containing SDS. The proteins were transferred to a nitrocellulose membrane and the Cre recombinase was identified using a monoclonal antibody against Cre (Sauer et al. Mol. Cell Biol. 7:2087–2096 (1987)). Ten of the cell lines tested had an immunologically reactive signal with an apparent migration corresponding to 38 kd. Control extract from 293 cells produced no signal at 38 kd. The concentration of Cre varied from 0.03 to 4 μM in the extracts. Assuming that one half of the volume of the cell is taken up by the nucleus, this corresponds to a nuclear Cre concentration of 30 μM in the cell lines with the highest concentration.

To determine if the Cre protein detected in the Western blot was functional, a recombination assay was carried out as follows. Each cell line was transfected with a plasmid carrying the β-galactosidase gene flanked by non-equivalent lox sites (pAdlox2β-gal). Approximately 24 hrs later the transfected cell cultures were infected with an Adenovirus (Adlox2) carrying the same two non-equivalent lox sites as pAdlox2β-gal. If recombination between the plasmid and the virus occurs at both lox sites, a new adenoviral vector carrying the β-galactosidase marker will be produced. Two days after infection the virus produced from each cell line was harvested and used to infect cells for detection of β-galactosidase activity by X-gal staining. The amount of recombinant virus produced in each cell line correlated well with the amount of Cre protein detected on the Western blots.

To further characterize the Cre-producing cell lines for both recombination and ability to support the growth of E1-deleted Adenovirus vectors, each cell line was separately infected with one of two different adenovirus vectors. The first viral vector was Ad β-gal, which carries a deletion of E1 and expresses β-galactosidase. This virus is insensitive to Cre recombinase and the level of β-galactosidase that it produces during infection reflects the infectivity of the cells and the amount of viral protein produced. The second viral vector was Adfloxβ-gal, which carries a β-galactosidase gene flanked by identical lox sites. The expression of β-galactosidase from the second virus is sensitive to the level of Cre recombinase because Cre-mediated recombination will result in excision of the β-galactosidase gene. All of the Cre-expressing cell lines produced more intense X-gal staining with Ad β-gal than did the parental 293 cell line. All of the Cre-expressing cell lines produced about 5 times more intense staining when infected with Ad β-gal than with Adfloxβ-gal. One cell line having the highest β-galactosidase expression with Ad β-gal, CRE8, was chosen for further experiments.

Example 4

Growth of Helper rAd Vector ψ5 on Cre-expressing Cell Line

To confirm that the ψ5 helper rAd is negatively selected on Cre-expressing cells, two types of experiments were carried out.

First, a mixture of ψ5 and a similar Ad virus without lox sites, AdΔ, was used to infect either 293 cells or CRE8 cells. Virus from each infection was purified and DNA isolated. The DNAs were digested with BsaBI and separated on 0.6% agarose gels containing ethidium bromide. The ratio of left end fragments of 2.8 kb and 2.2 kb, for AdΔ and ψ5 respectively, indicated the relative amount of each virus produced. For growth in 293 cells, the ratio was 60% ψ5 to 40% AdΔ; for CRE8 cells, 5% ψ5 and 95% AdΔ.

Second, the growth of ψ5 in 293 cells or CRE8 cells was compared to the growth of Adlox2 in the same cell lines. Adlox2 is similar to ψ5 but contains two non-equivalent lox sites rather than two equivalent lox sites. Equal viral yields were obtained in 293 cells, but the yield of ψ5 in CRE8 cells was 1/20 of the yield of Adlox2 in CRE8 cells.

Example 5

Construction of New Recombinant Adenoviruses with E1 Substitutions

Several different replicating vectors were prepared from pAdlox by inserting one of several different genes into the expression cassette. Genes inserted included β-galactosidase, nitrous oxide synthase, T7 RNA polymerase, and nicotinic acetylcholine receptor α and β subunits. The replicating vectors were digested with SfiI to release the ITR bounded fragment and each digested replicating vector was mixed with ψ5 DNA and used to transfect CRE8 cells. Plaques appeared after 3–4 days and viral lysates were prepared after 7 days. These lysates were used to infect CRE8 cells in a 10 cm dish. Packaged viral DNAs were prepared from the infected cells 2 days following infection. The DNAs were digested with BsaBI and the fragments separated on an agarose gel containing ethidium bromide. In each case, a new left end fragment appeared and the left end fragment corresponding to that from ψ5 was not detected. The recombinant viruses were also successfully tested for the expression of the substitute DNA.

Example 6

Production of Gutless Virus

6 μg each of SfiI digested ploxAβ and ψ5 DNA's were co-transfected into a 6 cm dish of CRE8 cells. After three days the cells were overlaid with agar, and after seven days another layer of agar was added with 0.8 mg/ml of X-gal. The following day, 12 blue plaques were selected and freeze-thaw lysates made from the cells in the plaques. The loxAβ gutless virus was then amplified on CRE8 cells by successive passage of the virus onto $10^4$, $10^5$, $10^6$ and finally $10^7$ cells. At each step we added enough ψ5 virus to insure that all of the cells were infected by the helper virus. Restriction analysis of packaged DNA from CRE8 cells infected with a portion of the virus from the $10^7$ cell lysates showed that ten out of twelve contained an appreciable amount of loxAβ DNA (data for the first six are shown in FIG. 5). The amount of loxAβ DNA varied from a few percent to 20 percent of the total amount of virus. In two cases there was a large amount of helper virus DNA, indicating that ψ5 had escaped selection. Two of the isolates were passaged further by infection into CRE8 cells without supplemental ψ5 virus. The amount of loxAβ DNA never increased above 25 percent, and in both cases the helper viruses too escaped selection.

To assess the integrity of the loxAβ virus, fragments produced from a ClaI digestion of several of the isolates were analyzed (FIG. 6). ClaI digestion produces five major fragments from loxAβ, all of which migrated at their predicted sizes.

Example 7

Mutation of ψ5 to Escape Selection

In order to determine the nature of the ψ5 virus after the transfection and amplification process, we plaque purified viruses from isolates 1 and 3 in FIG. 5 taking eight plaques for each isolate from which we prepared DNA. Restriction analyses of these DNA's demonstrate that many contain deletions (FIG. 7). Taking representative viruses, we amplified two segments containing the loxP sites by PCR and then sequenced the PCR products. The left loxP sites were intact. However, in all cases the right loxP site was missing.

To further analyze the stability of ψ5 in CRE8 cells, we passaged ψ5 virus through CRE8 cells. After eight passages, the virus began to grow well. Once again, we plaque purified isolates from the passaged virus and subjected the DNA to restriction analyses and sequencing. Out of ten viruses, one was still ψ5, the rest had deletions of one or the other of the loxP sites.

Example 8

Production and Amplification of LoxβA Virus in 293 Cells

Only the final growth of gutless virus need be under negative selection by Cre recombinase in CRE8 cells. The plasmid ploxβA can be converted into a gutless virus by co-transfection into 293 cells. As this process is very inefficient, the virus must be amplified by some means. The method we have used is a positive selection based on an expressed β-galactosidase gene in the gutless virus. β-galactosidase has been chosen to demonstrate the concept. The selection could be for the gutless virus or against the helper virus or a complementation for viral growth of both (see FIG. 8A). Ideally, unless the selection marker can be used therapeutically, it should be absent from the final therapeutic virus. This can be arranged by placing the marker between lox sites. These sites should be different from the lox site next to the packaging site so that they will not recombine. We have accomplished the selection by sorting on a FACS. The same result could be obtained by panning for an expressed extracellular membrane protein.

LoxβA virus was grown as follows. 6 μg each of ploxβA and ψ5 DNA's were cotransfected into 293 cells. After seven days the cells were suspended in their media and a freeze thaw lysate was prepared. 1 ml of the lysate was used to infect $2\times10^6$ 293 cells. At about 20 hours after infection the cells were removed from the dish by a brief treatment with trypsin, washed and loaded with florescein-digalactoside for one minute. The cells were then placed in chilled media and sorted on a FACstar cell sorter. Yield, 20,000 positive cells, which were then plated into 1 ml of tissue culture media and allowed to grow for 24 more hours. At twenty-four hours, the cells were suspended in their media and a freeze thaw/lysate was prepared. This lysate was used undiluted, to infect $2.8\times10^6$ more 293 cells. 60,000 β-galactosidase positive cells were recovered. A lysate was prepared from these cells which was used to infect $10^6$ cells. These were sorted and 600,000 cells were recovered.

At this point 25% of the virus was used to infect $10^7$ 293 cells. We prepared packaged DNA from these cells, digested it with BglII and analyzed the fragments by gel electrophoresis. The total amount of loxβA virus was 5% of the total. In an attempt to change the ratio of ψ5 to loxβA virus, we used small amounts of the virus to infect 293 cells then sorted the cells again. So we infected $2\times10^6$ 293 cells with either 3, 6 or 12 μl of the virus and 0.67, 1.3 and 3.4% of the cells were β-galactosidase positive, respectively. If the loxψA virus is as infectious as ψ5, then most of the positive cells should have received one of each virus. We recovered 47,000 cells after infection with 12 μl of virus, from which we prepared a lysate. This was amplified by infecting $2\times10^6$ 293 cells from which a lysate was prepared without sorting. Half of this lysate was used to infect $10^7$ 293 cells from which a 10 ml working stock of virus was made.

To determine the ratio of helper to gutless virus, and to see if the Cre mediated selection would still work, 1 ml of the working stock was used to infect $10^7$ 293 or CRE8 cells from which packaged DNA was prepared. The DNA's were digested with BglII and the fragments resolved by agarose gel electrophoresis (FIG. 9). From 293 cells, the loxβA was about 10% of the total viral DNA, and from CRE8 cells, the loxβA was about 50% of the DNA. This change results from a decrease in the amount of ψ5 rather than an increase in the amount of loxβA. Clearly the Cre mediated selection was functioning as designed.

Next a 1:1 mixture of loxβA:ψ5 viruses was prepared by infecting $10^7$ CRE8 cells with 1 ml of the working stock yielding a 10 ml enriched stock. 1 ml of this virus was then used to infect either $10^7$ 293 or CRE8 cells from which packaged DNA was prepared. These DNA's were subjected to restriction analysis with BglII. The composition of the virus was 10% loxβA when grown in 293, and 50% loxβA when grown in CRE8 cells. These results show that in 293 cells the loxβA virus grows less well than the ψ5 helper virus, and in CRE8 cells the viruses grow equally well.

5 ml of the enriched stock was used to infect $5\times10^7$ CRE8 cells to produce 50 ml of viral lysate. 22.5 ml of this lysate was used to infect $2\times10^8$ CRE8 cells. The resulting virus was purified by CsCl density gradient centrifugation. The purified virus was used to infect CRE8 cells at over a wide range of particles per cell. DNA was prepared from the packaged virus at each concentration, and restriction analysis was performed with BsaBI (FIG. 10). At this point, the ratio of loxβA to ψ5 virus had improved to almost 90% loxβA virus, and this result was essentially independent of the amount of virus used for infection.

In an effort to assess the integrity of the loxβA virus, the samples were digested with a battery of restriction enzymes. In each case the terminal right end fragment was missing and unexpected bands were present. Except for the terminal right fragment, all of the predicted fragments were present for each enzyme used. The simplest explanation of these data is that the right end of the loxβA virus contains an insertion of a variable amount of DNA.

Next the viral DNA was treated with BstBI. BstBI does not cut the helper virus and should cleave once near the right end of loxβA. The digest produced a ladder of bands which represented right ends with 3 to 7 kb of extra DNA. These fragments were excised from the gel, treated with NaOH to remove the terminal protein, and ligated into the pSP73 cloning vector. Several clones were partially sequenced. The insertions came from either end of the helper virus. In a further analysis step, the virus was serially passaged with a mixture of insertions through four cycles of growth in CRE8 cells and then DNA was prepared for restriction analysis with BstBI. After five passages, the insertion size was clustered around 7 kb and the smaller insertions were gone. In an independent preparation of loxβA virus, insertions of around 7 kb were also observed.

In contrast to the data shown in FIG. 9, the loxβA viruses with insertions are able to grow about ten times better than the helper virus in CRE8 cells. As the insertions come from either end of the helper virus, and there appears to be a strong selection based on the size of the insertion, it seems unlikely that any specific information in the insertion is involved. Rather, the higher yield of loxβA virus with insertions results from increasing the loxβA chromosome to the optimal size for adenovirus. These viruses should preferably be within a lower size limit of approximately 32 kb in order to maintain efficient packaging. In order to achieve efficient packaging of the recombinant virus, the minimum size is preferably within the range of 32 kb to 38 kb. The preferred minimum size of the virus is from 34 kb to 37 kb. Most preferred is the size of 35–36 kb. The optimum packaging size is that of the wild-type-roughly 36 kb. Recombinant Ad viruses that are smaller than 32 kb are not as stable, which creates significant problems for reliable delivery of the same recombinant vector for gene therapy. This discovery of the optimum packaging size is also important for manufacturing large quantities of the viral particles for commercial use, in which case packaging efficiencies on the order of wild type efficiencies are desired.

The fact that the same type of recombination event occurred both times we grew up the gutless virus further supports the finding of the minimum size for packaging efficiency and points to the insertion site as a hot spot for non-homologous recombination.

Example 9

New Helper Viruses

To lower the potential of homologous recombination, ψ5 was modified by deleting the CMV promoter, multiple cloning site, and SV40 poly adenylation site from the virus. The new helper virus, called ψ9, is identical to ψ5 except the DNA between the first PvuII site (at position 454 in Ad5)

and the Klenow treated ClaI site immediately before the second loxP site was removed. Additionally, a larger E3 deletion was incorporated (positions 28133 to 30818). The amount of ψ9 DNA encapsidated in CRE8 compared to 293 cells with Ad β-gal as a standard was 1/6.

Example 10

Effect of Phasing of LoxP Sites on Recombination

There are two versions of ψ9, the one described above and one called ψ9+17 with 17 bp of linker DNA inserted between the loxP sites. The center to center distance between the loxP sites is 301 bp for ψ9 and 318 bp for ψ9+17. Assuming 10.5 bp per helical turn, the sites are 28.66 and 30.28 turns apart, respectively. The relative encapsidation efficiencies were measured of these two viruses. ψ9+17 was encapsidated 1/2 as well as ψ9 (FIGS. 11A and 11B). These data indicate that phasing of the loxP sites is important for maximal recombination.

Example 11

New Packaging Sites

In the original definition of the Ad5 packaging site, two mutations which packaged at low efficiency were produced, A5 and B1. The B1 mutation (deletion of 271 to 356 in Ad5) was incorporated into the ψ5 background, creating a virus called ψ11. In a comparative growth assay, ψ11 was mixed with Ad β-gal at 20 to 1 and infected 293 and CRE8 cells. Packaged DNA was prepared from each cell type and a PCR analysis was performed on the DNA's (FIG. 12). For growth on 293 cells, ψ11 is about 1/80 of Ad β-gal, in agreement with published estimates. For growth in CRE8 cells, ψ11 was undetectable.

The packaging site from Ad5 has varied degree of relationship to the same region from other serotypes of adenovirus. Substitutions were prepared of the Ad5 packaging domain (194 to 454 in Ad5) with the equivalent regions from Ad7 (203 to 466), Ad12 (101 to 401) and Ad40 (101 to 374), and these substitutions were built into a ψ9 background. The Ad7 substitution was viable, creating ψ7. In a measurement of the relative encapsidation efficiency, ψ7 was encapsidated at 30 and 5.9% of a similar virus with a normal Ad5 packaging site when grown in 293 and CRE8 cells respectively (FIG. 13).

Example 12

Purification of Gutless Virus by Successive Passage Through Cre8

$10^8$ CRE8 host cell are infected with a 1:1 mixture of loxβA and ψ5 at a multiplicity of infection of 5 for the ψ5. The yield was $4 \times 10^{12}$ particles at 85% loxβA and 15% ψ5. This virus mixture was used to infect $10^8$ CRE8 cells at a multiplicity of 5 for the ψ5. The yield of virus was $4 \times 10^{11}$ and the amount of ψ5 was about 3%.

Example 13

Constructing New Recombinant Adenoviruses with Substitutions

As shown in FIG. 14, new recombinant adenoviruses with substitutions in the E1 region can be generated using ψ5 as a helper vector that supplies an adenoviral backbone, a replicating vector with a single recombination site, a loxP site, and a cre-expressing, E1A+, E1B+ host cell line. The cre recombinase catalyzes recombination between ψ5 and the replicating vector with a single loxP site, providing an efficient means to construct recombinant adenoviruses with substitute DNA in place of the E1 region.

The Cre-lox recombination technique for generating new recombinant adenovirus vectors with substitutions was compared to a popular overlap recombination method for production of recombinants. A series of recombinations between transfected adenovirus donor DNAs (helper rAd vectors) and replicating vectors and then prepared lysates 3, 7, 10, and 14 days after transfection and screened for the presence of lacZ-positive virus, using the FDG assay. These recombinations were used to examine the effects of two factors, the source of the donor DNA and the mechanism of recombination. First, either ψ5 viral DNA or pBHG10 plasmid DNA was transfected along with replicating vectors marked with lacZ genes. Second, ψ5 DNA was combined with lacZ-marked replicating vectors having either a loxP site for Cre-lox recombination or a 5.5-kb adenovirus fragment for overlap recombination. Recombination into ψ5 viral DNA by either method produced by lacZ virus by 4 days, with Cre-lox recombination being slightly more efficient. In contrast, overlap recombination into PBHG10 plasmid DNA required 10 days before lacZ virus appeared, and then it did so only when the linear replicating vector was used.

An important factor in the recombination process might be the topology of the replicating vector plasmid. To test this, pAdlox plasmids carring a β-galactosidase marker gene (pAdlox β-gal) either uncut or treated in various ways was transfected along with ψ5 viral DNA. After 3 days lysates were prepared and titered for β-galactosidase-positive virus by the FDG assay. All of the transfections produced recombinant virus but with a substantial variation in efficiency depending on the treatment of the plasmid. Cutting the pAdlox plasmid at both ITRs (SfiI) or at both ITRs plus cutting off the right ITR (SfiI) or at both ITRs plus cutting off the right ITR (SfiI plus ApaI) produced equally high yields of recombinant virus. Cutting the plasmid with ScaI such that the ITRs remained buried in the plasmid sequences reduced the yield to 17% of SfiI-cut plasmid, and circular plasmid produced the least amount of recombinant virus, at about 4% of the rate of plasmid cleaved at the ITRs.

Next, transfection was used to introduce the replicating vector plasmid and compared infection with transfection to introduce ψ5 DNA. Cells were transfected with the replicating vector and infected with ψ5 virus at various times relative to the infection. One sample was cotransfected as before. Virus produced from each sample was used to infect CRE8 cells. A restriction analysis was performed on the packaged DNA to monitor the ratios of the helper rAd vector and recombinant viruses. Contransfection of ψ5 and pAdlox β-gal produced a virtually helper-free stock of recombinant virus in 10 days. In contrast, infection of the helper rAd virus combined with transfection of the replicating vector plasmid produced less recombinant virus and a significant amount of helper contamination in a similar time frame.

In the foregoing experiment, there was very little rAd helper virus DNA in cotransfected samples after the second passage through CRE8 cells. To determine more precisely how effectively the helper virus was removed during successive passages through CRE8 cells, we took the virus mixture from the cotransfection and passed it two more times through CRE8 cells, making lysates at each passage. Lysates which were stained with X-Gal and neutral red to distinguish the recombinant virus plaques from ψ5 or mutant viruses were then diluted and infected into 293 cells for plaque analyses. The initial transfection (passage 1) contained 30% ψ5 virus. One passage through CRE8 cells reduced the ψ5 virus to 3%. A further passage through CRE8 cells reduced the concentration of donor virus to 0.2%. See Hardy et al., J. Virology, 71(3):1842–1849 (1997) (incorporated herein by reference).

All publications and patent applications mentioned in this specification are herein incorporated by reference to the same extent as if each individual publication or patent application was specifically and individually indicated to be incorporated by reference.

What is claimed is:

1. A recombinant adenovirus helper-dependent vector comprising:
   a) an adenovirus left inverted terminal repeat sequence (ITR);
   b) at least one recombination site located 3' to the adenovirus left ITR sequence;
   c) an adenovirus packaging sequence located 3' to the recombination site of (b);
   d) a first foreign DNA sequence located 3' to the adenovirus packaging sequence; and
   e) an adenovirus right ITR sequence located 3' to the foreign DNA sequence.

2. The helper-dependent vector of claim 1 which further comprises a pair of identical recombination sites in direct orientation with respect to each other that flank the first foreign DNA sequence of (d).

3. The helper-dependent vector of claim 1 which further comprises a second foreign DNA sequence located 3' to the first foreign DNA sequence of (d).

4. The helper-dependent vector of claim 1 which further comprises a second foreign DNA sequence flanked by a pair of identical recombination sites in direct orientation with respect to each other located 3' to the first foreign DNA sequence of (d).

5. The helper-dependent vector of claim 1, wherein when more than one recombination site is present, the recombination sites are different.

6. The helper-dependent vector of claim 1, wherein when more than one recombination site is present, the recombination sites are the same.

7. The helper-dependent vector of claim 1, wherein the first and second foreign DNA sequences together range in size from about 31 kb to about 37 kb.

8. The helper-dependent vector of claim 1, wherein the first foreign DNA sequence ranges in size from about 31 kb to about 37 kb.

9. The helper-dependent vector of claim 1, wherein the second foreign DNA sequence ranges in size from about 31 kb to about 37 kb.

10. The helper-dependent vector of claim 1, wherein the first foreign DNA sequence comprises a nucleotide sequence that expresses a gene product.

11. The helper-dependent vector of claim 1, wherein the vector ranges in size from about 32 kb to about 38 kb.

12. The helper-dependent vector of claim 1, wherein the recombination site comprises a lox sequence.

13. A recombinant adenovirus helper vector comprising:
   a) an adenovirus left ITR sequence;
   b) an adenovirus packaging sequence located 3' to the adenovirus left ITR sequence;
   c) at least one pair of identical recombination sites in direct orientation to each other located 3' to the adenovirus left ITR sequence, wherein each pair of recombination sites flank the adenovirus packaging sequence;
      i. wherein if more than one pair of recombination sites are present then the recombination sites are nested;
   d) at least one adenovirus gene sequence located 3' to one pair of identical recombination sites of, wherein the adenovirus gene sequence encodes an adenovirus gene product; and
   e) an adenovirus right ITR sequence located 3' to the adenovirus gene sequence.

14. The helper vector of claim 13, wherein:
   a) at least one adenovirus gene sequence of claim 13 (d) located 3' to the adenovirus left ITR sequence;
   b) the adenovirus packaging sequence of claim 13 (b) located 3' to the adenovirus gene sequence; and
   c) a pair of identical recombination sites in direct orientation to each other of claim 13 (c) located 3' to the adenovirus gene sequence, wherein each pair of recombination sites flank the adenovirus packaging sequence, and
      i. wherein if more than one pair of recombination sites are present then the recombination sites are nested.

15. The helper vector of claim 13, wherein each member of a pair of recombination sites of claim 13 (c) is in phase with each other.

16. The helper vector of claim 13, wherein a pair of recombination sites of claim 13 (c) comprises a pair of lox sequences.

17. The helper vector of claim 13, wherein the packaging sequence of claim 13 (b) is a synthetic packaging sequence.

18. The helper vector of claim 13, wherein the adenovirus packaging sequence of claim 13 (b) is from a different serotype than the encoded adenovirus proteins.

19. The helper vector of claim 13, wherein the adenovirus packaging sequence of claim 13 (b) contains a mutated nucleotide sequence.

20. The adenovirus packaging sequence of claim 19, wherein the mutated nucleotide sequence includes a deletion.

21. A recombinant adenovirus vector comprising:
   a) an adenovirus left ITR sequence;
   b) an adenovirus packaging sequence located 3' to the adenovirus left ITR sequence;
   c) a foreign DNA sequence located 3' to the adenovirus packaging sequence; and
   d) at least one recombination site located 3' to a foreign DNA sequence.

22. The recombinant adenovirus vector of claim 21, wherein the recombination site comprises a lox sequence.

23. A method for generating packaged recombinant adenovirus vectors by a recombination event comprising:
   a) introducing a recombinant adenovirus vector comprising an adenovirus left ITR, an adenovirus packaging sequence, a foreign DNA sequence, and at least one recombination site, and recombinant adenovirus helper vector of claim 13 into a recombinase-expressing host cell,
   b) propagating the recombinant adenovirus vector and the recombinant adenovirus helper vector in the recombinase-expressing host cell; and
   c) isolating the packaged recombinant adenovirus resolved vector generated from the recombination event.

24. A method for generating recombinant adenovirus helper-dependent vectors comprising:

a) introducing a recombinant adenovirus helper vector of claim 13 and a recombinant adenovirus helper-dependent vector into a first recombinase-expressing host cell,
  i. wherein the recombinant adenovirus helper-dependent vector comprises an adenovirus left ITR, at least one recombination site, an adenovirus packaging sequence, foreign DNA sequence, an adenovirus right ITR; and
  ii. wherein the recombination sites in the recombinant adenovirus helper vector and the recombinant adenovirus helper-dependent vector are identical;
b) propagating the recombinant adenovirus helper vector and recombinant adenovirus helper-dependent vector in the first recombinase-expressing host cell; and
c) isolating a packaged recombinant adenovirus helper-dependent vector.

25. The method of claim 24 further comprising:

a) introducing the packaged recombinant adenovirus helper-dependent vector into a second recombinase-expressing host cell; and b) isolating packaged recombinant adenovirus helper-dependent vectors.

26. The method of claim 24 or 25, wherein steps (a) and (b) are repeated at least once.

* * * * *